(12) United States Patent
Shah et al.

(10) Patent No.: US 12,693,279 B2
(45) Date of Patent: *Jul. 28, 2026

(54) CONCENTRATION SENSOR FOR PRECURSOR DELIVERY SYSTEM

(71) Applicant: Applied Materials, Inc., Santa Clara, CA (US)

(72) Inventors: Vivek B. Shah, Santa Clara, CA (US); Varoujan Chakarian, North Hills, CA (US); Upendra Ummethala, Cupertino, CA (US)

(73) Assignee: Applied Materials, Inc., Santa Clara, CA (US)

( * ) Notice: Subject to any disclaimer, the term of this patent is extended or adjusted under 35 U.S.C. 154(b) by 296 days.

This patent is subject to a terminal disclaimer.

(21) Appl. No.: 18/373,732

(22) Filed: Sep. 27, 2023

(65) Prior Publication Data
US 2024/0019410 A1    Jan. 18, 2024

Related U.S. Application Data

(63) Continuation of application No. 17/365,906, filed on Jul. 1, 2021, now Pat. No. 11,808,746.

(51) Int. Cl.
G01N 33/00        (2006.01)
C23C 16/52        (2006.01)
(Continued)

(52) U.S. Cl.
CPC ......... G01N 33/0016 (2013.01); C23C 16/52 (2013.01); G01F 1/74 (2013.01); G01N 11/02 (2013.01); G01N 33/0073 (2013.01)

(58) Field of Classification Search
CPC .............. C23C 16/4481; C23C 16/52; C23C 16/45561; C23C 16/4482;
(Continued)

(56) References Cited

U.S. PATENT DOCUMENTS

| | | | |
|---|---|---|---|
| 4,341,107 | A | 7/1982 | Blair |
| 6,772,072 | B2 | 8/2004 | Ganguli et al. |
| | | (Continued) | |

FOREIGN PATENT DOCUMENTS

| | | |
|---|---|---|
| CN | 108699688 A | 10/2018 |
| EP | 0370311 A2 | 5/1990 |
| | (Continued) | |

OTHER PUBLICATIONS

PCT International Search Report and Written Opinion for International Application No. PCT/US2022/035352 mailed Oct. 19, 2022, 11 pages.

(Continued)

*Primary Examiner* — Timothy P Graves
(74) *Attorney, Agent, or Firm* — Lowenstein Sandler LLP

(57)        ABSTRACT

First sensor data indicative of a first mass flow rate of a first gas flowing to a vaporization chamber is received. The vaporization chamber includes a compound and is to transition the compound into a gaseous state. Second sensor data indicative of a second mass flow rate of a second gas including the compound and the first gas flowing out of the vaporization chamber is received. Third sensor data indicative of a third mass flow rate of the compound into the vaporization chamber is received. The first sensor data, the second sensor data, and the third sensor data is processed using a trained machine learning model to determine an estimated concentration of the compound within the second gas. At least one of a) modifying a flow rate of the first gas or b) providing the predicted concentration for display by a graphical user interface (GUI) is performed.

20 Claims, 9 Drawing Sheets

(51) Int. Cl.
*G01F 1/74* (2006.01)
*G01N 11/02* (2006.01)

(58) Field of Classification Search
CPC ... C23C 16/45544; C23C 16/448; G01F 1/76;
G01F 1/74; G01N 33/0016; G01N 11/02;
G01N 33/0073
See application file for complete search history.

(56) References Cited

U.S. PATENT DOCUMENTS

| | | |
|---|---|---|
| 8,951,478 B2 | 2/2015 | Chu et al. |
| 2005/0019026 A1 | 1/2005 | Wang et al. |
| 2005/0095859 A1* | 5/2005 | Chen ..................... C23C 16/52 |
| | | 438/689 |
| 2006/0032444 A1* | 2/2006 | Hara .................. C23C 16/4481 |
| | | 427/248.1 |
| 2016/0004259 A1 | 1/2016 | Salinas et al. |
| 2016/0090651 A1 | 3/2016 | Ashihara et al. |
| 2016/0097127 A1 | 4/2016 | Lenz |
| 2017/0168036 A1* | 6/2017 | Albright ............ G01N 33/0073 |
| 2017/0335450 A1 | 11/2017 | Collins et al. |
| 2021/0032751 A1 | 2/2021 | White et al. |

FOREIGN PATENT DOCUMENTS

| | | |
|---|---|---|
| EP | 3450588 A1 | 3/2019 |
| JP | 2013133542 A | 7/2013 |
| JP | 6868951 B2 | 5/2021 |
| KR | 20150124871 A | 11/2015 |
| WO | 2005-010230 A1 | 3/2005 |

OTHER PUBLICATIONS

Extended European Search Report for European Application No.
22834082.4 mailed Jan. 20, 2026, 07 Pages.

* cited by examiner

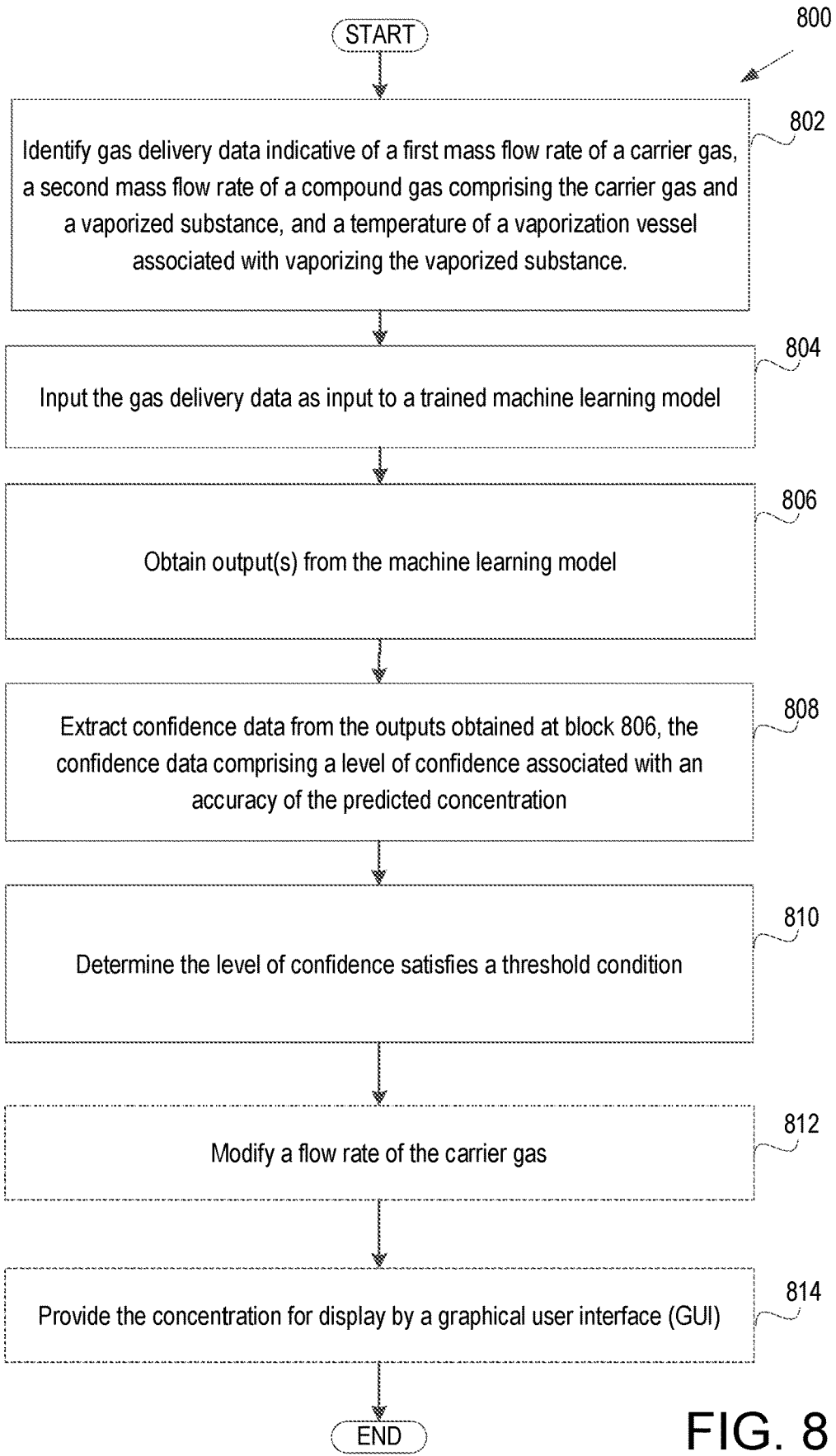

800

START

Identify gas delivery data indicative of a first mass flow rate of a carrier gas, a second mass flow rate of a compound gas comprising the carrier gas and a vaporized substance, and a temperature of a vaporization vessel associated with vaporizing the vaporized substance.

802

Input the gas delivery data as input to a trained machine learning model

804

Obtain output(s) from the machine learning model

806

Extract confidence data from the outputs obtained at block 806, the confidence data comprising a level of confidence associated with an accuracy of the predicted concentration

808

Determine the level of confidence satisfies a threshold condition

810

Modify a flow rate of the carrier gas

812

Provide the concentration for display by a graphical user interface (GUI)

814

END

FIG. 8

CONCENTRATION SENSOR FOR PRECURSOR DELIVERY SYSTEM

RELATED APPLICATIONS

This continuation application claims priority to U.S. Non-provisional patent application Ser. No. 17/365,906, filed on Jul. 1, 2021, the contents of which is incorporated by reference in its entirety.

TECHNICAL FIELD

This instant specification generally relates to gas delivery to a process chamber. More specifically, the instant specification relates to a sensor for measuring concentration of a precursor within a process gas.

BACKGROUND

Integrated circuits have evolved into complex devices that include millions of transistors, capacitors, and resistors on a single chip. The evolution of chip design continually calls for faster circuitry and greater circuit density demanding increasingly precise fabrication processes. The precision processing of substrates call for precise control of temperature, flow rate, and pressure in the delivery of fluids used during processing.

Chemical vapor deposition (CVD) and atomic layer deposition (ALD) are vapor deposition processes used to form or deposit various materials on a substrate. In general, CVD and ALD processes involve the delivery of gaseous reactants to the substrate surface where a chemical reaction takes place under temperature and pressure conditions favorable to the thermodynamics of the reaction. The type and composition of the layers that may be formed using a CVD process or an ALD process are limited by the ability to deliver a chemical reactant or precursor to the substrate surface. Various solid and/or liquid precursors have been successfully used during CVD and ALD applications by delivering the precursors within a carrier gas.

A carrier gas is in some cases passed through a heated vessel or canister, such as an ampoule or bubbler, which contains a volatile liquid precursor under conditions conducive to vaporize the precursor. In other cases, a carrier gas is passed through a heated vessel containing a solid precursor under conditions conducive to sublime the solid precursor. The sublimation process is typically performed in a vessel loaded or filled with a solid precursor, and the vessel walls are heated to sublime the solid precursor material while producing a gaseous precursor. In either case, the carrier gas combines with the vaporized precursor to form a process gas which is drawn from the vessel via dedicated conduits or gas lines to a reaction chamber.

BRIEF DESCRIPTION OF THE DRAWINGS

FIG. 8 depicts a flow diagram of one example method for determining a concentration of a vaporizable substance using a trained machine learning model, in accordance with some implementation of the present disclosure.

SUMMARY

Figures 1A, 1B:
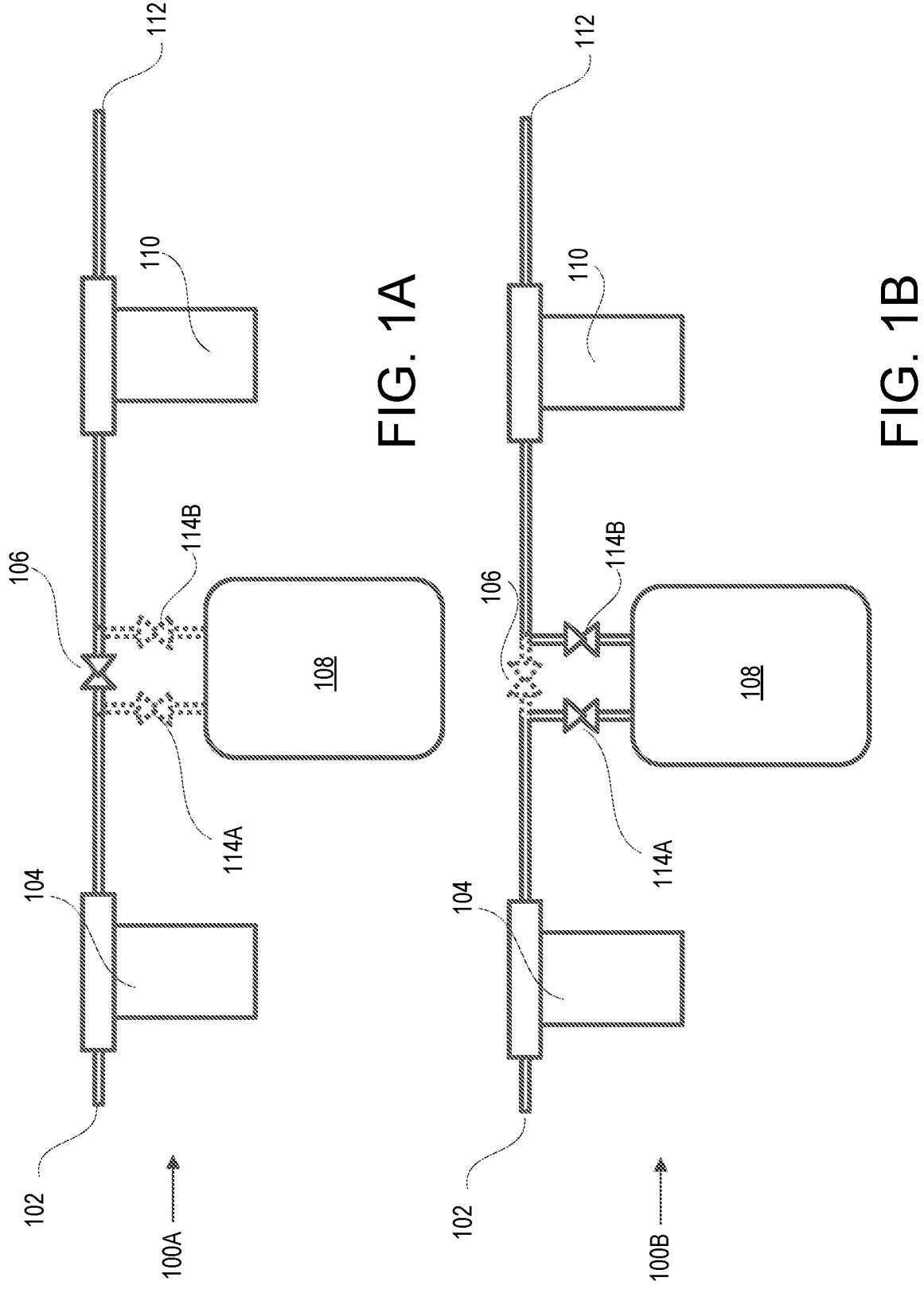
FIG. 1A-B illustrates exemplary embodiments of a concentration sensor assembly, according to some embodiments.

In some embodiments, a concentration sensor assembly includes a vaporization chamber having a compound. The vaporization chamber transitions (e.g., via sublimation or vaporization) the compound to a gas. The concentration sensor assembly may further include a first flow path connected to the vaporization chamber. The first flow path may direct a first gas to the vaporization chamber. A second flow path is coupled to the vaporization chamber. The second flow path directs a second gas out of the vaporization chamber. The second gas includes the compound gas and the first gas. A first sensor is disposed along the first flow path. The first sensor measures first data indicative of a first mass flow rate of the first gas within the first flow path. A second sensor is disposed along the second flow path. The second sensor measures second data indicative of a second mass flow rate of the second gas within the second flow path. The concentration sensor may further include a computing device coupled to the first sensor and the second sensor. The computing device determines a concentration of the compound within the second gas based on the first data and the second data.

In some embodiments, a precursor concentration delivery system includes a vaporization vessel. The vaporization vessel includes a precursor. A first flow path is connected to the vaporization vessel. The first flow path directs a carrier gas into the vaporization vessel. A second flow path is connected to the vaporization vessel. The second flow path directs a process gas out of the vaporization vessel. The process gas includes the carrier gas and the precursor. A process chamber is connected to the second flow path. The second flow path directs the process gas to the process chamber. A first flow meter is disposed along the first flow path. The first flow meter measure first data indicative of a first flow rate of the carrier gas within the first flow path. A second flow meter is disposed along the second flow path. The second flow meter measures second data indicative of a second flow rate of the process gas within the second flow path. A computing device is coupled to the first flow meter and the second flow meter. The computing device determines a concentration of the precursor within the process gas based on the first data and the second data.

In some embodiments, a method includes receiving, by a processing device from a first sensor, first data indicative of a first mass flow rate of a carrier gas. The processing device receives, from a second sensor, second data indicative of a second mass flow rate of a compound gas including the carrier gas and a vaporized substance. The processing device receives, from a third sensor, third data indicative of a temperature of a vaporization vessel associated with vaporizing the vaporized substance. The processing device determines a concentration of the vaporized substance within the compound gas based on the first data, the second data, and the third data. The method may include modifying a flow rate of the carrier gas. The method may include providing the concentration for display by a graphical user interface (GUI).

DETAILED DESCRIPTION

As noted previously, chemical vapor deposition (CVD) and atomic layer deposition (ALD) are vapor deposition processes used to form or deposit various materials on a substrate. In general, CVD and ALD processes involve the delivery of gaseous reactants to the substrate surface where a chemical reaction takes place under temperature and pressure conditions favorable to the thermodynamics of the reaction. The type and composition of the layers that may be formed using a CVD process or an ALD process are limited by the ability to deliver a chemical reactant or precursor to the substrate surface. Various solid and/or liquid precursors have been successfully used during CVD and ALD applications by delivering the precursors within a carrier gas.

A carrier gas is in some cases passed through a heated vessel or canister, such as an ampoule or bubbler, which contains a volatile liquid precursor under conditions conducive to vaporize the precursor. In other cases, a carrier gas is passed through a heated vessel containing a solid precursor under conditions conducive to sublime the solid precursor. The sublimation process is typically performed in a vessel loaded or filled with a solid precursor, and the vessel walls are heated to sublime the solid precursor material while producing a gaseous precursor. In either case, the carrier gas combines with the vaporized precursor to form a process gas which is drawn from the vessel via dedicated conduits or gas lines to a reaction chamber.

Conventionally, a vapor deposition process that utilizes a solid precursor may suffer several problems. While a solid precursor should be provided enough heat to be sublimed into a gaseous state, the solid precursor may decompose if exposed to too much heat. Metal-organic solid precursors, which are usually very expensive, are especially susceptible to thermal decomposition and generally should be maintained within narrow temperature and pressure ranges during a sublimation process. Once decomposed, solid precursors may contaminate the remaining precursor in the vessel, the delivery system of conduits and valves, and/or the processing chamber, as well as a substrate. Furthermore, overheating a solid precursor may provide too high of a precursor concentration within the process gas, which may lead to wasted precursor that is not used or condensation of the precursor within the delivery lines or on the substrate.

Alternatively or additionally, the solid precursor may not sublime if exposed to too little heat. As the carrier gas is flowed through the vessel and impacts the solid precursor, particulates from the solid precursor may become entrained in the carrier gas and transferred into the process chamber. These solid or liquid particulates may become a source of contamination for the delivery system, processing chamber, and/or substrate. The problem of particulate contamination has been addressed in the art by including a liquid carrier material mixed with a solid precursor. However, the mixture of the liquid carrier material and the solid precursor may not be conducive outside of limited temperature and pressure ranges since the liquid carrier material may be evaporated and become a contaminant within the delivery system, the processing chamber, and/or on the substrate.

Conventionally, a precursor (as well as other liquid) induces chemical reactions by introducing various types of reactive gases into the processing (or reactive) chambers during semiconductor fabrication. In CVD processing, there is a growing preference to use liquid precursors instead of gases. The popularity of liquid precursors is based in part on physical properties that render them less harmful, flammable, corrosive, and poisonous than gaseous ones. For example, one of the more common liquids used in fabricating semiconductor devices is Tetraethylorthosilicate (TEOS), which is frequently substituted for silane. With TEOS, conformal silicon dioxide ($SiO_2$) films with no detectable defects can be deposited with better step coverage and with far less hazard than when silane is used. In metal organic CVD (MOCVD) processes, liquid precursors for metals such as copper are often used because gaseous precursors are not available.

Because liquid precursors (and other process liquids) are first liquid, they are converted to a gaseous state to deliver the precursor as a gas through a delivery line. Faults in the manufacturing operation or delivery line environment, particularly that impact temperature and pressure, can lead to condensation of some of the gas in a delivery line. Such condensation can absorb and carry particles into the processing chamber and deposit the particles on the substrate, causing particle defects on the substrate and any resultant manufactured device.

Methods for detecting and recognizing potential problems in a precursor delivery system by determining an amount of precursor or concentration of precursor being used within the process gas is disclosed. Many of the above referenced problems may be remedied or otherwise mitigated with high resolution control of flow rates within a precursor delivery system. There is a need for an efficient and cost effective concentration sensor that performs under robust measuring conditions. For example, some conventional concentration sensors or monitors may include high cost specialized equipment that are not capable of measuring concentration of various precursors flowing with a variety of carrier gases. Conventional concentration sensors often involve expensive equipment such as optical sensors that are pre-calibrated and rely on specific equipment specifications and/or configurations for different carrier gases and/or precursors.

Aspects and implementations of the present disclosure address these and other shortcomings of existing technology by providing an assembly, system, and/or method for determining a concentration of a compound (e.g., a precursor) within a compound gas (e.g., a process gas). In some embodiments, the relationship between pressure, mass flow rate, and vaporization rate are employed to determine mass flow rate of a gas before and after a compound is integrated through vaporization. For example, mass flow meters may be calibrated and configured to measure flow rates before and after compound (e.g., precursor) vaporization to determine how much (e.g., concentration) of the compound is flowing through a point of a gas delivery system. In another example, the change in density (i.e., vapor pressure multiplied by molecular weight) is leveraged in combination with the inverse relationship between vapor pressure and molecular weight to determine concentration of the vaporized compound knowing that the molecular mass of the carrier is likely unchanged.

In an exemplary embodiment, a concentration sensor assembly includes a vaporization chamber including a compound. The vaporization chamber vaporizes the compound. The concentration sensor assembly may further include a first flow path connected to the vaporization chamber. The first flow path may direct a first gas (e.g., a carrier gas) to the vaporization chamber. A second flow path is coupled to the vaporization chamber. The second flow path directs a second gas (e.g., the carrier gas plus a precursor gas) out of the vaporization chamber. The second gas includes the compound gas and the first gas. A first sensor is disposed along the first flow path. The first sensor measures first data indicative of a first mass flow rate of the first gas within the first flow path. A second sensor is disposed along the second flow path. The second sensor measures second data indicative of a second mass flow rate of the second gas within the second flow path. The concentration sensor may further include a computing device coupled to the first sensor and the second sensor. The computing device determines a concentration of the compound within the second gas based on the first data and the second data. The computing device may be, for example, a programmable logic controller (PLC), a system on a chip (SoC), a computer, a field programmable gate array (FPGA), or other type of computing device.

In an exemplary embodiment, a precursor concentration delivery system includes a vaporization vessel. The vaporization vessel includes a precursor. A first flow path is connected to the vaporization vessel. The first flow path direct a carrier gas into the vaporization vessel. A second flow path is connected to the vaporization vessel. The second flow path directs a process gas out of the vaporization vessel. The process gas includes the carrier gas and the precursor. A process chamber is connected to the second flow path. The second flow path directs the process gas to the process chamber. A first flow meter is disposed along the first flow. The first flow meter measures first data indicative of a first flow rate of the carrier gas within the first flow path. A second flow meter is disposed along the second flow path. The second flow meter measures second data indicative of a second flow rate of the process gas within the second flow path. A computing device is coupled to the first flow meter and the second flow meter. The computing device determines a concentration of the precursor within the process gas based on the first data and the second data.

In an exemplary embodiment, a method includes receiving, by a processing device or computing device from a first sensor, first data indicative of a first mass flow rate of a carrier gas. The processing device receives, from a second sensor, second data indicative of a second mass flow rate of a compound gas including the carrier gas and a vaporized substance. The processing device receives, from a third sensor, third data indicative of a temperature of a vaporization vessel associated with vaporizing the vaporized substance. The processing device determines a concentration of the vaporized substance within the compound gas based on the first data, the second data, and the third data. The method may include modifying a flow rate of the carrier gas. The method may include providing the concentration for display by a graphical user interface (GUI). For example, the computing device may include a display to which the determined concentration may be output.

Aspects of the present disclosure provide various technological advantages and improvements over conventional system. As previously outlined, methods for measuring concentration can be difficult, lack reliability, and/or generally be inefficient. In some embodiments, concentration sensor assemblies are capable of measuring concentration of a compound (e.g., precursor) within a gas (e.g., a carrier gas) where the compound and the gas are capable of being modified. For example, a carrier gas may be selectively used for a specific purpose (e.g., to reduce mass flow rate, improve chemical interaction on a surface of the surface, greater capability with a precursor, etc.) without requiring physical equipment reconfigurations. Sensor may be calibrated with updated data for the carrier gas and the precursor used and concentration measurements may be performed.

FIGS. 1A-B illustrate exemplary embodiments of a concentration sensor assembly 100A-B, according to some embodiments. FIG. 1A illustrates the concentration sensor assembly 100A operating in a bypass or calibration mode. FIG. 1B illustrates the concentration sensor assembly 100B operating in a gas delivery mode. As shown in FIGS. 1A-B the concentration sensor assembly 100A-B include a first flow path 102. The first flow path 102 directs a first gas to or past a vaporization chamber 108 (e.g., ampoule, vessel, etc.) that may be coupled to the first flow path through a chamber leg 114A. The vaporization chamber 108 may house a compound (e.g., a solid and/or liquid precursor) that may be transitioned (e.g., through vaporization, sublimation, etc.) into a gaseous state (e.g., vapor). A second flow path 112 may be coupled to the vaporization chamber through chamber leg 114B. The second flow path 112 may direct a second gas out of the vaporization chamber. The second gas may include the first gas and the compound in a gaseous state.

As shown in FIG. 1A-B, a first sensor 104 may be disposed along the first flow path 102. The first sensor 104 may measure first data indicative of a first mass flow rate of the first gas within the first flow path. For example, the sensor 104 may include a mass flow meter, a mass flow controller (MFC), a volume flow meter, a pressure sensor, a temperature sensor, a mass sensor, and/or other sensor to measure a state of the first gas within the first flow path 102. In some embodiments the sensor 104 measures mass flow rate directly. In other embodiments, the sensor 104 measures one or more of volumetric flow, molecular mass, and/or pressure of the first gas within the first flow path 102. The data measured by sensor 104 may be communicated to a computing device (not shown) for data processing.

A second sensor 110 may be disposed along the second flow path 112. The second sensor 110 may measure second data indicative of a second mass flow rate of the second gas (e.g., process gas or compound gas) exiting the vaporization chamber 108. For example, the sensor 110 may include a mass flow meter, an MFC, a volume flow meter, a pressure sensor, temperature sensor, mass sensor, and/or other sensor to measure a state of the second gas within the second flow path 112. In some embodiments, the sensor 110 measures mass flow rate directly. In other embodiments, the sensor 110 measures one or more of volumetric flow, molecular mass, and/or pressure of the first gas within the second flow path 112. The data measured by second sensor 110 may be communicated to a computing device (not shown) for data processing.

As shown in FIG. 1A, the concentration sensor assembly 100A includes a bypass flow path 106. The bypass flow path 106 may be used by the carrier gas to bypass the vaporization chamber 108 and avoid aggregating the vaporized compound. The bypass flow path 106 may be utilized to calibrate the second sensor 110. For example, the second sensor 110 may be calibrated for linearity and/or zero offset such as to improve an accuracy of a mass flow rate measurement and/or overall concentration determination.

As described, the data measured by the first sensor 104 and the second sensor 110 may be received and processed by a computing device. The following gas property may be utilized to take mass flow measurement and calculate the concentration:

$$\text{Vapor pressure} \propto \frac{1}{\text{Molecular weight}} \qquad \text{(Equation 1)}$$

In some embodiments, the computing device determines the change in density (e.g., Vapor pressure multiplied by molecular weight) between the measurement of the first sensor 104 and the measurement of the second sensor 110. For example, a gas may travel through the first flow path with a molecular weight of 28 grams per mole (g/mol). This may be measured by determining at sensor 104 that the first gas is flowing at 250 standard cubic centimeter per minute (sccm) with a pressure of 100 torr. After passing through the vaporization chamber 108 and picking up the compound, a gas mixture including the first gas (e.g., carrier gas) and the compound (e.g., precursor) flow through the second flow path. The second sensor may measure an average molecular weight of 30.89 g/mol which is about 10% greater than the carrier gas alone. The average molecular weight may be determined by measuring a flow rate of about 275 sccm and a pressure of 100 torr. The percentage increase of the carrier gas with the vaporized compound is indicative of the concentration of the compound within the compound gas.

It should be noted that the method for calculating concentration is species independent. Conventional concentration sensors like optical sensors are recalibrated and manufactured to measure predetermined species specification windows with limits on density, molecular mass, flow rate, etc. In contrast, embodiments allow for species independent calculations that can work for various gases (e.g., carrier gases and process gasses) and various compounds (e.g., precursors).

In some embodiments, the first sensor 114 further includes a mass flow controller to control the flow of the first gas within the first flow path 102. The computing device may send instructions to one or more flow rate controllers to alter a flow rate of the first gas within the first flow path 203 and/or the second gas within the second flow path 112 based on compound concentration determinations.

In some embodiments, the concentration sensor assembly 100A-B may include a first valve disposed along the first flow path. The first valve may be integrated with or otherwise coupled to first sensor 104. The first valve may be selectively opened and closed to alter a first flow rate of the first gas. For example, the first valve may be controlled by the computing device (e.g., based on compound concentration determinations). In some embodiments, the concentration sensor assembly 100A-B may include a second valve disposed along the second flow path 112. The second valve may be integrated with or otherwise coupled to second sensor 110. The second valve may be selectively opened and closed to alter a second flow rate of the second gas. For example, the second valve may be controlled by the computing device (e.g., based on compound concentration determinations).

In some embodiments, as will be discussed extensively in association with other figures, the compound may comprise a precursor for processing a substrate. Additionally or alternatively, as will be discussed further in other embodiments, the concentration sensor assembly 100A-B may include a third flow path coupled to the vaporization chamber 108. The third flow path may direct the compound in the vaporization chamber 108. A third sensor may be disposed along the third flow path. The third sensor may measure third data indicative of a third mass flow rate (e.g., similar to sensors 104 and/or 110). The computing device may calculate the concentration of the compound within the second gas based further on the third data. The computing device may further determine a depletion rate of the compound within the vaporization chamber 108 based on the determined concentration within the second gas.

In some embodiments, as will be discussed further in other embodiments, the concentration sensor assembly 100A-B may include a sensor to measure data indicative of a state of the vaporization chamber. For example, the sensor may measure the temperature, pressure, etc. within the chamber. The computing device may calculate the concentration of the compound further based on the state of the vaporization chamber.

Figure 2:
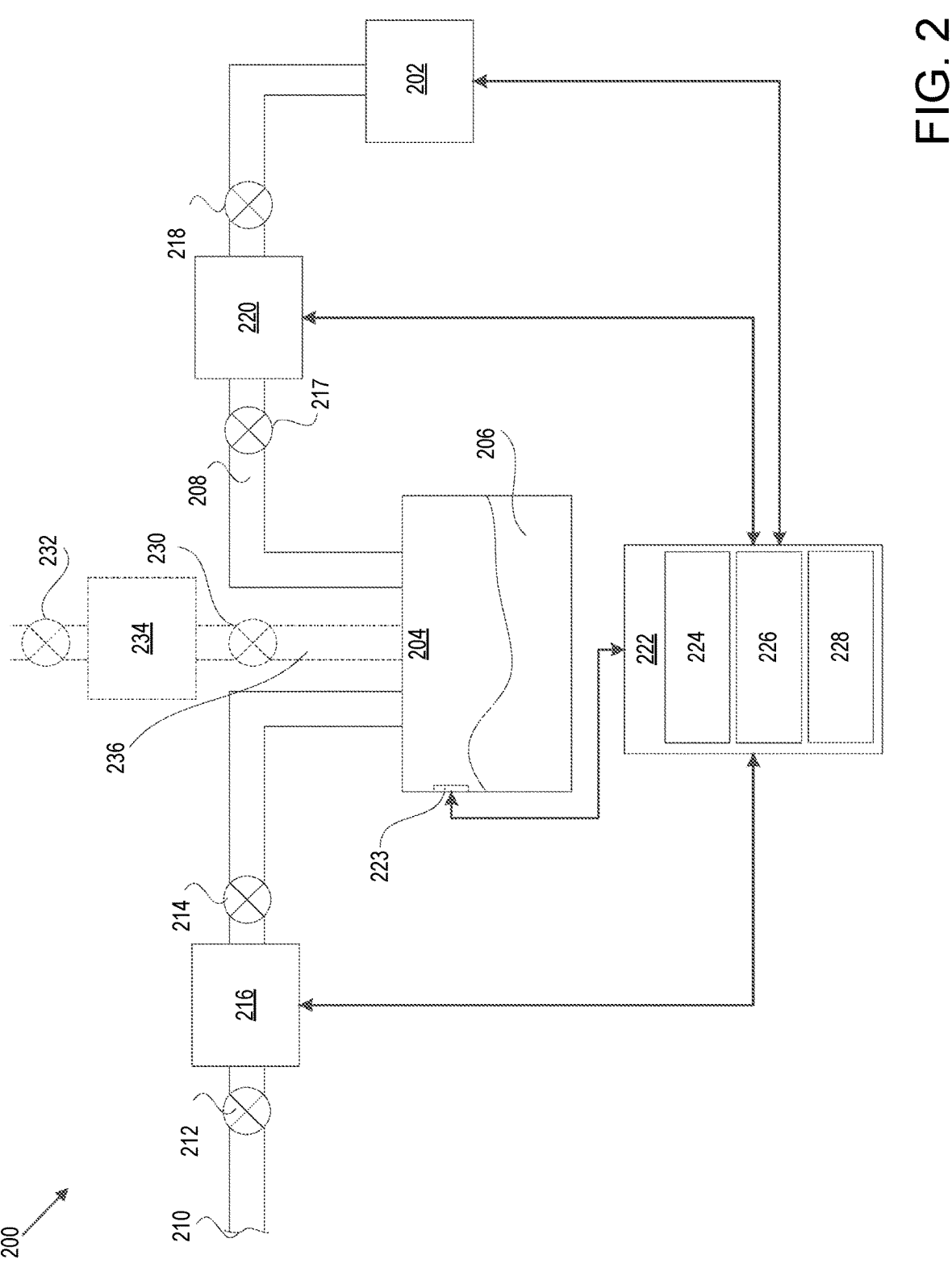
FIG. 2 illustrates a gas delivery system, according to some embodiments.

FIG. 2 illustrates a gas delivery system 200, according to some embodiments. As shown in FIG. 2, the gas delivery system 200 includes a process chamber 202. The process chamber 202 may be any suitable semiconductor process chamber, such as a chemical vapor deposition (CVD) chamber, atomic layer deposition (ALD) chamber, or etch chamber. For some embodiments, the etch chamber may be suitable to perform tantalum nitride (TaN) ALD.

The gas delivery system 200 transports a precursor 206 from a vessel 204 to the process chamber 202 via a process gas 208. Typically, the precursor 206 changes state from a solid or liquid to a gas (or vapor) in the vessel 204 by a sublimation or vaporization process. The sublimation or vaporization process may be initiated by any suitable well-known technique. For example, the precursor 206 may be heated to a predetermined temperature or mixed with a bubbling liquid within the vessel 204. For some embodiments, the temperature of the vessel 124 may be controlled in an effort to regulate the sublimation and/or vaporization process.

A first flow path may be coupled to the vessel 204 (e.g., a vaporization vessel). The first flow path may direct a carrier gas into the vessel 204. The carrier gas 210 flows through one or more of valve 212, flow meter 216, and/or second valve 214 into the vessel 204 and mixes with the vaporized precursor 206. A second flow path may be coupled to the vessel 204. The second flow path may direct a process gas 208 out of the vessel 204. The second flow path is to direct the process gas 208 to the process chamber 202. For example, the process gas 208 flows out of the vessel 204 and transports the vaporized precursor 206 through one or more of valve 217, flow meter 220, and/or valve 218 to the process chamber 202. For some embodiments, the gas delivery system 200 may include a bypass line, for example, from the valve 214 to valve 217 or an equivalent flow path bypassing the vessel. The bypass line may allow the carrier gas 210 to flow directly to the process chamber such as to calibrate flow meter 220 or to purge the process chamber 202, for example.

The material of the precursor 206 may be chosen based on the particular process to be performed in the process chamber 202. For example, the precursor 206 may be a metal organic material, such as tungsten carbonyl (W(CO)6) to deposit a metal film (W) on a wafer. As another example, the precursor 206 may be pentadimethylamino-tantalum (PD-MAT) to form a film comprising tantalum. As another example, the precursor 206 may also be a precursor to deposit a layer of dielectric material on the wafer, or xenon difluoride (XeF$_2$), for example, to deliver fluoride to an etch chamber. The carrier gas 210 is typically chosen based on the precursor 206. For example, argon may be chosen as the carrier gas 210 if the precursor 206 is tungsten carbonyl. The carrier gas 210 may be an inert gas, such as argon or helium, and may be reactive or non-reactive with the precursor 206.

To facilitate understanding, the gas delivery system 200 is illustrated as delivery of only one gas to the process chamber 202. However, the gas delivery system 200 may deliver additional gases (i.e. carrying additional precursors) to the process chamber 202 and multiple gas delivery systems are also contemplated. It will also be appreciated by those skilled in the art that the gas delivery system 200 may also comprise additional component not illustrated, such as bypass valves, purge valves, flow controllers, and/or temperature controllers.

The vessel 204 may be any suitable container, for example, capable of withstanding the pressure and temperature used to sublime and/or vaporize the precursor 206. For some embodiments, the container may comprise a bubbler. As previously described, in conventional processing system, it may be difficult to determine an amount (e.g., a concentration) of precursor 206 that is disposed within the process gas 208 and being delivered to the process chamber 202. Additionally or alternatively, in conventional system it may be difficult to determine an amount of precursor 206 remaining in the vessel 204.

In some embodiments, as shown in FIG. 2, the gas delivery system 200 includes a flow meter 216 disposed along the first flow path. Flow meter 216 measures first data indicative of a first flow rate (e.g., a mass flow rate or a volume flow rate) of the carrier gas 210 (e.g., within the first flow path). The gas delivery system 200 includes flow meter 220 disposed along the second flow path. The flow meter 220 measure a flow rate of the process gas 208 (e.g., within the second flow path). One of flow meter 216 and/or flow meter 220 may calculate a mass flow rate and/or a volume flow rate of the carrier gas 210 and process gas 208, respectively. For example, densities, pressure, and volumetric measurement may be performed to determine a mass flow rate and/or a volume flow rate. As used herein, mass flow rate refers to a mass amount of gas within a given volume (e.g., passing through a region of a flow meter), volume flow rate refers to a volume of gas (e.g., carrier gas or process gas) flowing in a determined area, and material or substance density refers to a mass of material or substance in a given volume of the gas delivery system 200. The data taken from flow meters 216, 220 may be transmitted to computing device 222. In some embodiments, flow meters 216, 220 may include or otherwise operate in a manner similar to mass flow controllers (MFCs). For example, flow meters 216, 220 may control a flow of the carrier gas and/or the process gas within the respective flow paths.

As shown in FIG. 2, the vessel 204 may include a sensor 223. Sensor 223 may be a sensor to perform measurement of the vessel 204 such as pressure, temperature, density, etc. The measurements may be associated with a sublimation and/or vaporization process. For example, the sensor may measure a current temperature of the vessel 204. The data taken by sensor 223 may be transmitted to computing device 222.

As shown in FIG. 2, the gas delivery system 200 may include a computing device 222. The computing device may receive data from one or more of flow meters 216, 220 and/or sensor 223. The computing device 222 may be coupled to flow meters 216, 220, sensor 223, and/or processing chamber 202. In some embodiments, the computing device 222 may be coupled to one or more valves 212, 214,

217, 218 of the gas delivery system. The computing device 222 may include a rackmount server, a router computer, a personal computer, a mainframe computer, a laptop computer, a tablet computer, a desktop computer, an FPGA, an SoC, a PLC, etc. The computing device 222 may include computing hardware, firmware, and/or software (e.g., one or more features described in association with FIG. 6).

The computing device 222 may include a concentration tool 224, a system control module 226, and/or a precursor monitor 228. The concentration tool 224 receives first data indicative of a first flow rate of the carrier gas 210 and second data indicative of a second flow rate of the process gas 208. The concentration tool may calculate a concentration of the precursor 206 within the process gas 208 based on these measurements. As discussed previously, relationships between flow rate, density, and vaporization may be employed to determine a relative concentration of the precursor within the process gas 208. As will be discussed further in other embodiments, the computing device may receive data indicative of flow rate of additional flow path as appropriate and may aggregate this data with first and second data to perform updated concentration calculation and make further determinations. In some embodiments, as will be further discussed, sensor data indicative of a state of the vessel 204 may also be received and incorporated into the precursor 206 concentration determined.

The system control module 226 monitors and controls system methods, such as controlling flow rates of gases (e.g., carrier gas or process gas), adjusting the state of the vessel (e.g., changing temperature, pressure, etc.), and/or carrying out process chamber procedures (e.g., a CVD process or an ALD process). Precursor 206 concentration determination (e.g., by the concentration tool 224) may be incorporated into decisions made by the system control module 226. For example, if a precursor concentration is higher than a threshold level the system control module 226 may cause a flow of the carrier gas to increase (e.g., opening valve 212 or 214 to increase flow rate) or cause a flow rate of a precursor into the vessel to be decreased (e.g., partially closing valves 230, 232).

In some embodiments, the system control module 226 may determine whether a precursor concentration meets a threshold criteria and cause process operations associated with the process chamber to be modified. For example, process operations within the chamber may cease until the precursor concentration fails to meet the threshold condition. In another example, process steps may be performed under different parameters based on the determine precursor concentration (e.g., higher temperature, longer etching durations, deposition durations, etc.)

The precursor monitor 228 may receive precursor concentration calculations (e.g., from concentration tool 224) and make determinations associated with the precursor. In some embodiments, the precursor monitor 228 may determine a rate of depletion of the precursor 206 within the vessel 204 based on the concentration of the precursor 206 within the process gas 208. For example, a flow rate and concentration may be used to determine a rate of depletion of the precursor 206. In another example, a flow rate indicative of a precursor input rate such as the flow of precursor 206 from a precursor storage into the vessel 204, may be accounted and contributed to a calculated depletion rate of the precursor 206.

In some embodiments, as described previously, the precursor 206 includes a precursor for substrate processing within the processing chamber 202. For example, the precursor 206 may be used as a part of a CVD process or an ALD process.

In some embodiments, a first valve 212, 214 is disposed along the first flow path and a second valve 217, 218 is disposed along the second flow path. The first valve 212, 214 may selectively open and/or close to alter a first flow rate of the carrier gas 210. The second valve 217, 218 may selectively open and/or close to alter a second flow rate of the process gas 208.

In some embodiments, the gas delivery system 200 may include a third flow path (indicated by the dashed features). The third flow path may include valves 230, 232, flow meter 234 and a path that includes a push gas 236. The third flow path may direct the precursor 206 into the vessel 204 via a push gas 236. Flow meter 234 measures third data indicative of a third flow rate of the precursor within the third flow path. The computing device 222 may calculate the concentration of the precursor 206 further using the third data. For example, the rate of the precursor and push gas may account for a portion of the mass flow rate measured by flow meter 220.

In another embodiment, the third flow path may direct a second carrier gas into the vessel 204. Flow meter 234 may measure third data indicative of a third flow rate of the second carrier gas within the third flow path. The computing device 222 may calculate the concentration of the precursor further using the third data (e.g., the flow rate of the second carrier gas). For example the flow rate of the second carrier gas may account for a portion of the mass flow rate measured by the flow meter 220.

In some embodiments, as discussed previously, the vessel 204 may include a sensor 223 to measure a state of the vessel 204. For example, the sensor 223 may be a temperature sensor capable of measuring data indicative of a temperature of the vessel 204. The computing device 222 may calculate the concentration of the precursor (e.g., using concentration tool 224) using the third data.

Figure 3:
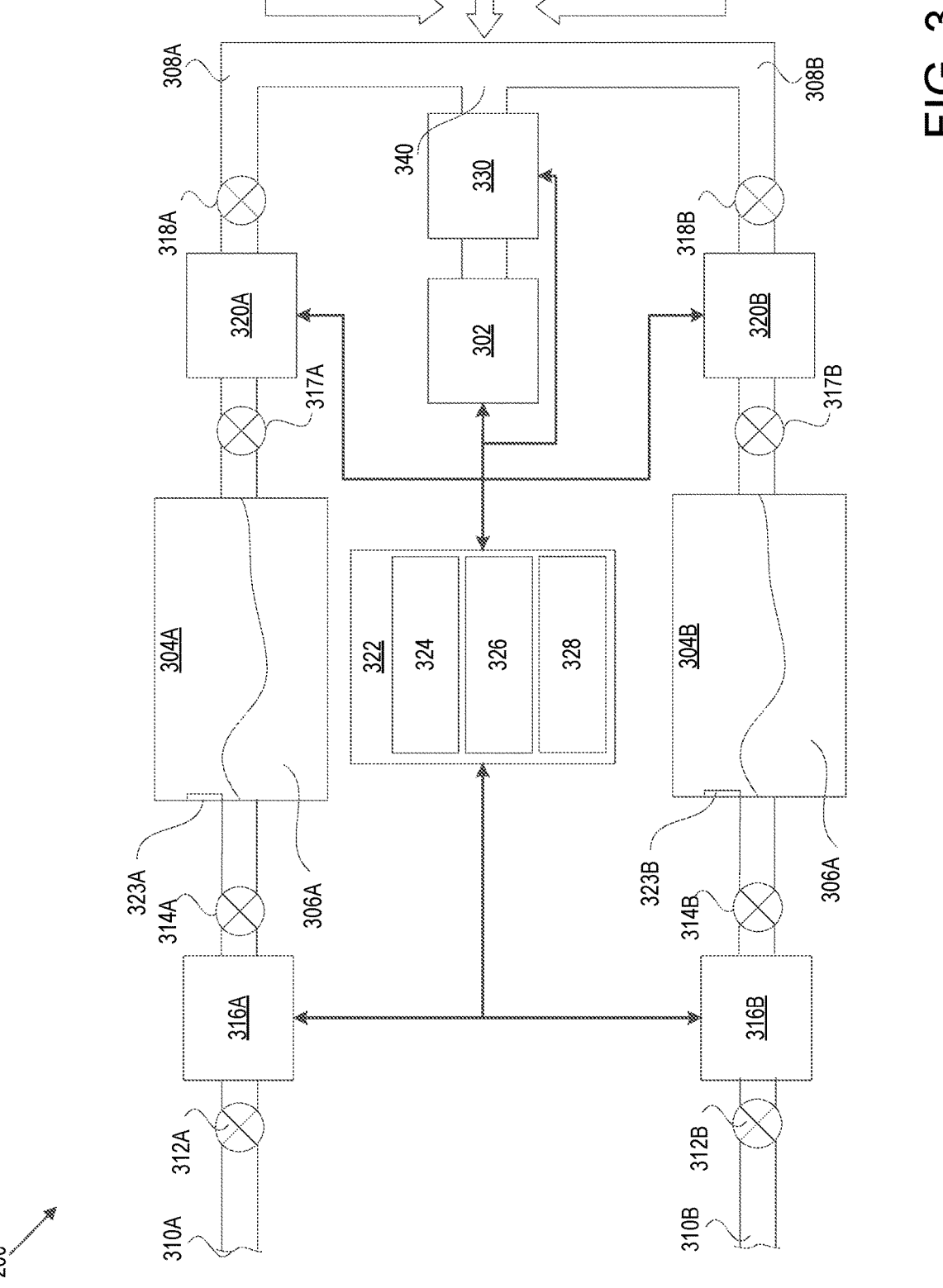
FIG. 3 illustrates a gas delivery system, according to some embodiments.

FIG. 3 illustrates a gas delivery system 300, according to some embodiments. The gas delivery system 300 may be a further embodiment from the gas delivery system 200 discussed and illustrated in associated with FIG. 2. The gas delivery system 300 may include multiple concentration sensor assemblies working together to determine sub concentrations and overall concentration of one or more precursors within the gas delivery system 300.

As shown in FIG. 3, a first flow branch may include a first carrier gas source 310A, flow meter 316A, vessel 304A, precursor 306A, and flow meter 320A. The functional and/or disposition of each of these element may include features and descriptions described in association of other figures (see FIG. 3). Flow meter 316A measures data indicative of a mass flow rate of a first carrier gas. Flow meter 320A measure data indicative of a mass flow rate of a process gas disposed along the first flow branch. Computing device 322 may determine a concentration of precursor 306A within a first process gas at junction 308A.

As shown in FIG. 3, a second flow branch may include a second carrier gas source 310B, flow meter 316B, vessel 304B, precursor 306B, and flow meter 320B. The functional and/or disposition of each of these element may include features and descriptions described in association of other figures (see FIG. 3). Flow meter 316B measures data indicative of a mass flow rate of a second carrier gas. Flow meter 320B measure data indicative of a mass flow rate of a process gas disposed along the first flow branch. Computing device 322 may determine a concentration of precursor 306B within a second process gas at junction 308A.

The first process gas interacts with the second process and mixes together at junction 340. The gas delivery system 300 includes a mass flow meter 330 that measure the mass flow rate of a compound gas including the first process gas and the second process gas. The mass flow rate of the compound gas may be performed as described herein.

As shown in FIG. 3, the computing device 322 may be coupled to flow meters 316A, 320A, 316B, 320B, and 330. Computing device may determine a relative concentration one or more of the first precursor 306A and/the second precursor 306B within the compound gas. The computing device may determine concentration using methodology as described herein (e.g., method 500 of FIG. 5). A concentration of each precursor may be determined relative to the compound gas as a whole. It should be noted that FIG. 3 depicts a system having two flow branches having identical elements. However, each branch may include more or less elements such as valves 312A-B, 314A-B, 317A-B, 318A-B, and temperature sensor 323A-B depending on the embodiment employed. Additionally, more than two carrier gases and precursor combinations may be employed to determine the concentration of a precursor within a compound gas such as having three or more carrier gas and/or precursor combinations.

As described in other embodiments, the computing device 322 may include a concentration tool 324, a system control module 326, and/or a precursor monitor 328. The concentration tool 324 receives first data indicative of one or more of a first flow rate of the first carrier gas and/or the second carrier gas and second data indicative of a second flow rate of the first process gas and/or the second process gas. The concentration tool may calculate a concentration of the first precursor 206A within the first process gas, a concentration of the second precursor 206B within the second process gas, and each of the first precursor 206A and the second precursor 206B within the compound gas including the first process gas and the second process gas. As discussed previously, relationships between flow rate, density, and vaporization may be employed to determine a relative concentration of each precursor. As will be discussed further in other embodiments, the computing device may receive data indicative of flow rate of additional flow path as appropriate and may aggregate this data to perform updated concentration calculation and make further determinations. In some embodiments, as will be further discussed, sensor data indicative of a state of the vessel 304 may also be received and incorporated into the determined precursor concentration.

The system control module 326 monitors and controls system methods, such as controlling flow rates of gases (e.g., carrier gases or process gases), adjusting the state of the vessels 304A-B (e.g., changing temperature, pressure, etc.), and/or carrying out process chamber procedures (e.g., a CVD process or an ALD process). Precursors 306A-B concentration determinations (e.g., by the concentration tool 324) may be incorporated into decisions made by the system control module 326. For example, if a precursor 306A-B concentration is higher than a threshold level the system control module 326 may cause a flow of the carrier gas to increase (e.g., opening valves 312A-B or 314A-B to increase flow rate) or cause a flow rate of a precursor 306A-B into the vessels 304A-B to be decreased (e.g., partially closing valves 312A-B, 314A-B).

In some embodiments, the system control module 326 may determine that a precursor concentration meets threshold criteria and cause process operations associated with the process chamber 302 to be modified. For example, process operations within the chamber may cease until the precursor concentration fails to meet the threshold condition. In another example, process steps may be performed under different parameters based on the determine precursor concentration (e.g., higher temperature, longer etching durations, deposition durations, etc.)

The precursor monitor 328 may receive precursor 306A-B concentration calculations (e.g., from concentration tool 324) and make determinations associated with the precursor. In some embodiments, the precursor monitor 328 may determine a rate of depletion of the precursors 306A-B within the vessels 204A-B based on the concentration of the precursors 306A-B within each process gas. For example, a flow rate and concentration may be used to determine a rate of depletion of the precursors 306A-B. In another example, a flow rate indicative of a precursor input rate such as the flow of precursors 306A-B from a precursor storage into the vessels 304A-B, may be accounted and contributed to a calculated depletion rate of the precursors 306A-B.

Figure 4:
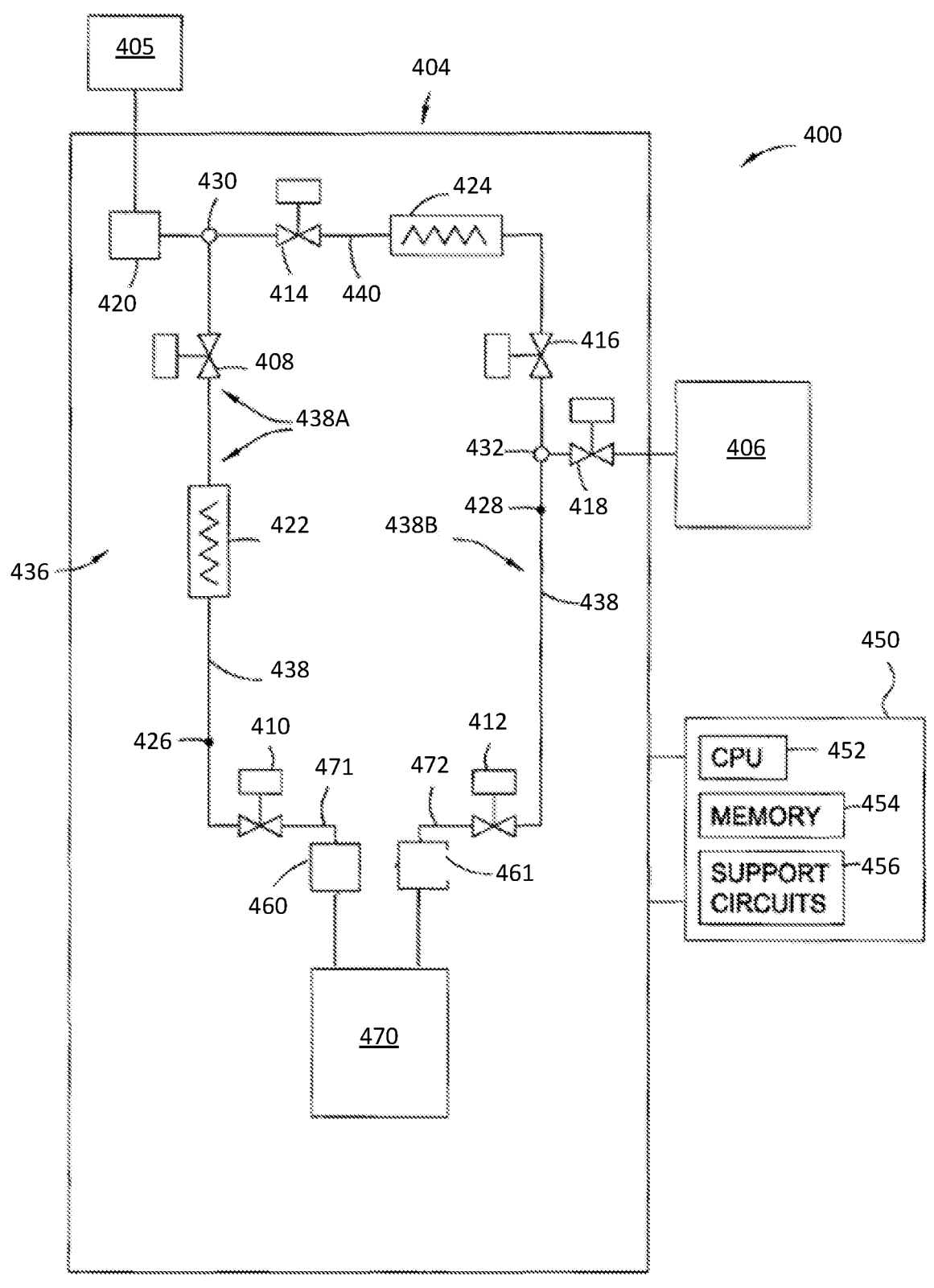
FIG. 4 illustrates a precursor delivery system, according to some embodiments.

FIG. 4 illustrates a precursor delivery system 400, according to some embodiments. The precursor delivery system 400 may be suitable for producing a process gas containing a chemical precursor and generally includes process chamber 406 and carrier gas source 405 coupled to gas panel 404, the components of the latter being controlled by a controller 450 or computing device. Gas panel 404 generally controls the rate and pressure at which various process and carrier gases are delivered to process chamber 406 Process chamber 406 may be a chamber to conduct vapor deposition processes or thermal processing containing a vaporized chemical precursor in liquid, gaseous, or plasma state. Process chamber 406 is generally a chemical vapor deposition (CVD) chamber, an atomic layer deposition (CVD) chamber, an atomic layer deposition (ALD) chamber, or a derivative thereof.

In the configuration illustrated in FIG. 1, controller 450 includes central processing unit (CPU) 452, memory 454, and support circuits 456. Central processing unit 452 may be one of any form of computer processor that can be used in an industrial setting for controlling various chambers and subprocessors. Memory 454 is coupled to CPU 452 and may be open or more of readily available memory such as random access memory (RAM), read only memory (ROM), flash memory, compact disc, floppy disk, hard disk, or any other form of local or remote digital storage. Support circuits 456 are coupled to CPU 152 for supporting CPU 152 in a conventional manner. These circuits include cache, power supplies, clock circuits, input/output circuitry, subsystems, and the like. The controller 450 may be and/or include a computing device such as a personal computer, a server computer, a programmable logic controller (PLC), a micro-controller, and so on. The controller 450 may include one or more processing devices, which may be general-purpose processing devices such as a microprocessor, central processing unit, or the like. More particularly, the processing device may be a complex instruction set computing (CISC) microprocessor, reduced instruction set computing (RISC) microprocessor, very long instruction word (VLIW) micro-processor, or a processor implementing other instruction sets or processors implementing a combination of instruction sets. The processing device may also be one or more special-purpose processing devices such as an application specific integrated circuit (ASIC), a field programmable gate array (FPGA), a digital signal processor (DSP), network processor, or the like. The controller 450 may include a data storage device (e.g., one or more disk drives and/or solid state drives), a main memory, a static memory, a network interface, and/or other components. The controller 450 may execute instructions to perform any one or more of the methodologies and/or embodiments described herein. The instructions may be stored on a computer readable storage medium, which may include the main memory, static memory, secondary storage and/or processing device (during execution of the instructions).

Fluid delivery circuit 436 is generally intended to fluidly couple carrier gas source 405, ampoule 470, and process chamber 406. Carrier gas source 405 may be a local vessel, remote vessel or a centralized facility source that supplies the carrier gas throughout the facility (e.g., in-house gas supply). Carrier gas source 405 typically supplies a carrier gas such as nitrogen, hydrogen, argon, helium, or combinations thereof. Fluid delivery circuit 436 typically includes a flow controller 420 disposed between carrier gas source 405 and junction 430 and is adapted to modulate the flow rate of carrier gas or other fluids through fluid delivery circuit 436. Flow controller 420 may be a proportional valve, a modulating valve, a needle valve, a regulator, a mass flow controller (MFC) or the like. Junction 430 separates fluid delivery circuit 436 into gas generation line 438 and bypass line 440. Junction 432 rejoins gas generation line 438 and bypass line 440 before connecting to process chamber 406.

Gas generation line 438 includes ampoule inlet leg 438A, ampoule outlet leg 438B, valve 408, 410, 412, sensors 426, 428, disconnect fitting 462, 463, and heater 422. Ampoule inlet leg 438A fluidly coupled the inlet of ampoule 470 to carrier gas source 405 and to bypass line 440. Ampoule outlet leg 438B fluidly coupled the outlet of ampoule 470 to process chamber 406 and to bypass line 440. Valve 408, 410, 412 are typically remotely controllable shut-off valve that serve to divert the flow of fluids within fluid delivery circuit 436 and/or are used to selectively isolate the various components within fluid delivery circuit 436 to facilitate removal, replacement and/or service of an isolated component, including sensors 426, 428, heater 422, and ampoule 470. Valves 408, 410, 412, as well as valves 414, 416, 418 (described below in conjunction with bypass line 440) are generally pneumatically or electronically controlled and the internal wetted surfaces thereof are fabricated from materials compatible with the process and other fluids handled by fluid delivery circuit 436. Typically, valves 408, 410, 412, 414, 416, and 418 are actuated in response to a signal from a controller 450 or computing device to coordinate the delivery of gases through fluid delivery circuit 436. Sensors 426, 428 are generally adapted to detect the temperature of a process and/or carrier fluid flowing through gas generation line 438, such as a thermocouple disposed against a conduit of gas generation line 438.

Bypass line 440 generally includes valves 414, 416 and heater 424 and serves to fluidly couple process chamber 406 and carrier gas source 405 without the use of gas generation line 438 or ampoule 470. Valve 418 is generally coupled between junction 432 and process chamber 406 and may be used to isolate process chamber 406 from fluid delivery circuit 436. Heaters 422, 424 are resistive heating elements or other heat sources adapted to heat a flow of fluid, such as a carrier gas, flowing through gas generation line 438 and bypass line 440, respectively.

Flow meter 460 is disposed between junction 471 and the ampoule 470. Flow meter 461 is disposed between junction 472 and the ampoule. Flow meters 460 and 470 may include sensors capable of measuring data indicative of mass flow rate. For example, pressure, volume flow rate, density, may all be measured. Flow meter 460 measures a flow of a carrier gas prior to passing through ampoule 470. Flow meter 461 measures a flow of the process gas (e.g., the carrier gas and a precursor) after passing through the ampoule 470. The flow measurement may be received by the CPU 452. The CPU may calculate a concentration of the precursor within the process gas based on the measured mass flow rate of the carrier gas and the mass flow rate of the process gas. Additionally, in some embodiments, the ampoule 470 may include a sensor to measure the state of the ampoule such as temperature, pressure, etc. The measured state of the ampoule 470 may be received and further used to calculate the concentration of the precursor within the process gas.

Ampoule 470 may include a bubble, a canister, and other terms know in the art to describe containers designed and used to store, transport and distribute chemical precursors. Ampoule 470 may have a variety of sizes and geometries. Ampoule 470 may have a volume capacitance of a chemical precursor within a range from 0.5 L to about 10 L and more typically from about 1.2 L to about 4 L. In one example, ampoule 470 has a volume capacitance of a chemical precursor of about 2.5 L. Chemical precursors within the ampoule 470 include liquid, solid and gaseous precursors, preferably in liquid or fluid-like states at predetermined temperatures and/or pressures. For example, a chemical precursor may exist in the solid state at room temperature, but melts to the liquid state upon being heated to a predetermined temperature within the ampoule 470. In another example, the majority of a chemical precursor may remain in the solid state in the ampoule 470, but is heated to an elevated temperature during processing such that a small amount of the solid precursor sublimates directly into vapor. In another example, a chemical precursor may exist in the gaseous state at ambient pressure, but condenses to the liquid state upon being pressurized to a predetermined pressure within the ampoule 470.

Solid chemical precursors may be used to form process gases including tantalum precursors, such as pentakis (dimethylamido) tantalum (PDMAT; Ta(NMe$_2$)$_5$), pentakis (diethylamido) tertiaryamylimido-tris (dimethylamido) tanalum (TAIMATA, ($^t$AmylN)Ta(NMe$_2$)$_3$, where $^t$Amyl is the tertiaryamyl group (C$_5$H$_{11}$— or CH$_3$CH$_2$C(CH$_3$)$_2$—), or derivative thereof. In one embodiment, the PDMAT has a low halide content (e.g., Cl, F, I, or Br). The PDMAT may have a halide concentration of less than about 100 ppm. For example, the PDMAT may have a chlorine concentration of less than about 100 ppm, preferably, less than about 20 ppm, more preferably less than about 5 ppm, and more preferably, less than about 1 ppm, such as about 100 ppb or less.

Other solid chemical precursors that may be used to form process gases through a sublimation process include xenon difluoride, nickel carbonyl, and tungsten hexacarbonyl, or derivatives thereof. In other embodiments, liquid chemical precursors may be evaporated to form process gases within ampoules described herein. Some of the liquid chemical precursors that may be used to form process gases include tungsten precursors, such as tungsten hexafluoride (WF$_6$), tantalum precursors, such as tantalum (PDEAT; Ta(NEt$_2$)$_5$), pentakis(methylethylamido) tantalum (PMEAT; Ta(NMeEt)$_5$), tertbutylimino-tris(dimethylamino) tantalum (TBTDMT, $^t$BuNTa(NMe$_2$)$_3$), tertbutylimino-tris(diethylamino) tantalum (TBTDET, $^t$BuNTa(NEt$_2$)$_3$), tertbutylimino-tris(methylethylamino) tantalum (TBTMET, $^t$BuNTa(NMeEt)$_3$), or derivatives thereof, titanium precursors, such as titanium tetrachloride (TiCl$_4$), tetrakis(dimethylamino) titanium (TDMAT, (Me$_2$N)$_4$Ti)), tetrakis(diethylamino) titanium (TEMAT, (Et$_2$N)$_4$Ti)), or derivatives thereof, ruthenium precursors, such as bis(ethylcyclopentadienyl) ruthenium ((EtCp)$_2$Ru), hafnium precursors, such as tetrakis(dimethylamino) hafnium (TDMAH, (Me$_2$N)$_4$Hf)), tetrakis(diethylamino) hafnium (TDEAH, (Et$_2$N)$_4$Hf)), tetrakis(methylethylamino) hafnium (TMEAH, (MeEtN)$_4$Hf)), or derivatives thereof, and aluminum precursors, such as 1-methylpyrolidrazine:alane (MPA, MeC$_4$H$_3$N:AlH$_3$), pyridine:alane (C$_4$H$_4$N:AlH$_3$), alkylamine alane complexes (e.g., trimethylamine:alane (Me$_3$N:AlH$_3$), triethylamine:alane (Et$_3$N:AlH$_3$), dimethylethylamine:alane (Me$_2$EtN:AlH$_3$)), trimethylaluminum (TMA, Me$_3$Al), triethylaluminum (TEA, Et$_3$Al), tributylaluminum (Bu$_3$Al), dimethylaluminum chloride (Me$_2$AlCl), diethylaluminum chloride (Et$_2$AlCl), dibutylaluminum hydride (Bu$_2$AlH), dibutylaluminum chloride (Bu$_2$AlCl), or derivatives thereof.

During processing, a carrier gas flows from carrier gas source 405 through fluid delivery circuit 436 to ampoule 470. The carrier gas may be heated by heater 422, ampoule 470 may be heated to a target temperature, or in some applications, both the carrier gas and ampoule 470 may be heated. During processing, valves 414 and 416 are closed, directing all carrier gas flow to process chamber 406 via gas generation line 438 and ampoule 470.

Figure 5:
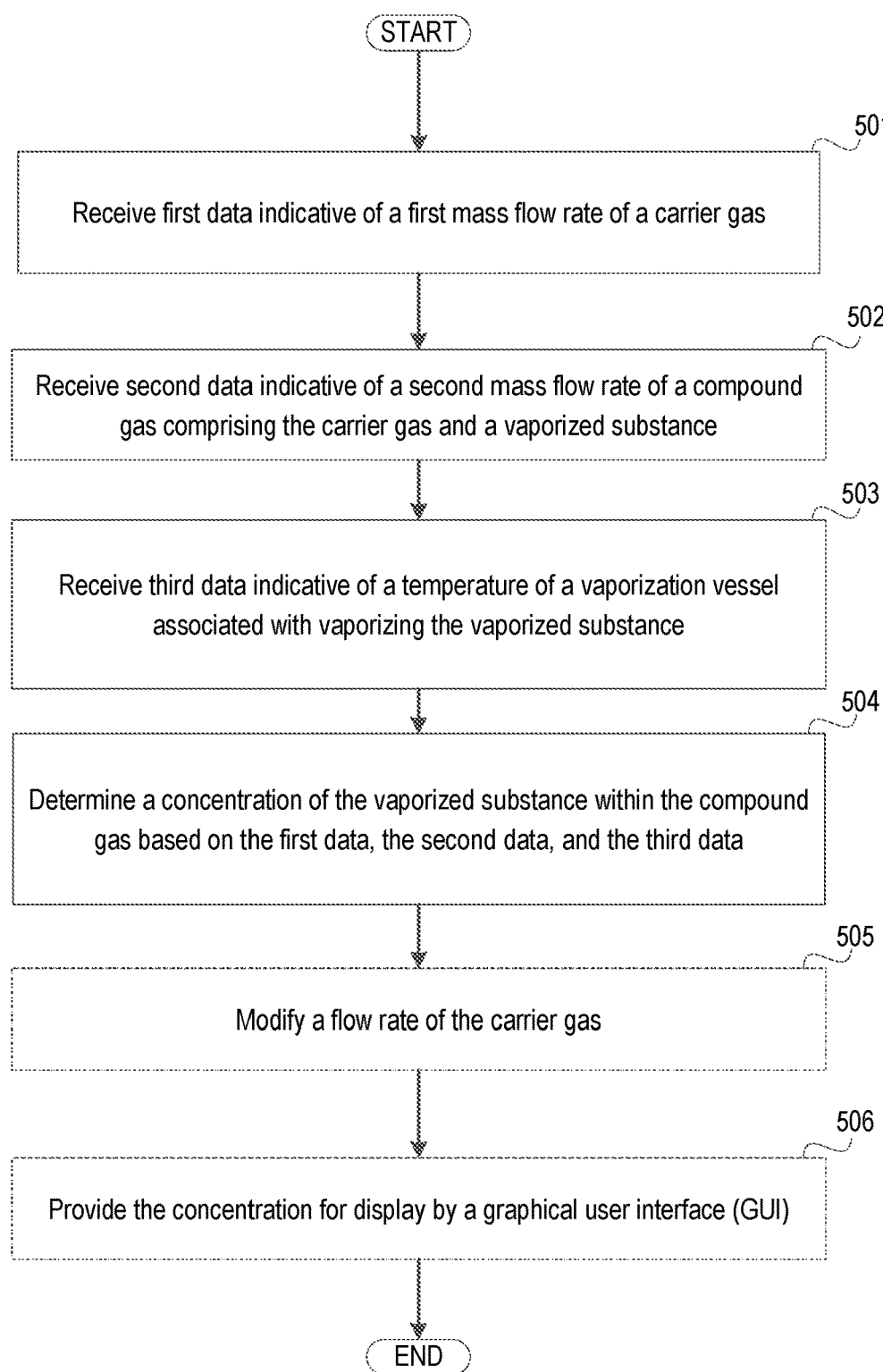
FIG. 5 is a flow chart of a method for determining concentration of a precursor, according to some embodiments.

FIG. 5 is a flow chart of a method 500 for determining concentration of a precursor, according to some embodiments. Method 500 may be performed by processing logic that may include hardware (e.g., circuitry, dedicated logic, programmable logic, microcode, processing device, etc.), software (such as instructions run on a processing device, a general purpose computer system, or a dedicated machine), firmware, microcode, or any combination thereof. In some embodiments, method 500 may be performed by computing device 222 of FIG. 2.

Referring to FIG. 5, method 500 is associated with determining concentration of a compound (e.g., precursor) in a gas delivery system (e.g., a precursor delivery system).

At block 501, processing logic receives first data indicative of a first mass flow rate of a carrier gas. The first data may be raw sensor data such as flow rate of the carrier gas, molecular weight of the carrier gas, and/or pressure of the carrier gas at a metrology location of a flow path of the carrier gas. The first data may be measured by one or more devices (e.g., sensors) discussed herein. The first data may be measured in a pressure controlled environment. For example, the system may be designed to maintain a constant pressure of the carrier gas throughout a measurement region.

At block 502, processing logic receives second data indicative of a second mass flow rate of a compound gas. The compound gas includes the carrier gas and a vaporized substance (e.g., precursor). The second data may be raw sensor data such as flow rate of the compound gas, molecular weight of the compound gas, and/or pressure of the compound gas. The second data may be measured by one or more devices (e.g., sensors), as discussed herein. The second data may be measured in a pressure controlled environment. For example, the system may be designed to maintain a constant pressure of the carrier gas and the compound gas throughout a measurement region.

In some embodiments, one or more of the first sensor and/or the second sensor include a mass flow rate controller. The computing device may send instructions to the first sensor and/or the second to alter a flow rate of the carrier gas and/or the compound gas. As is discussed herein, the flow control may be based on concentrations measurements and/or determination made by the processing device.

At block 503, processing logic receives third data indicative of a temperature of a vaporization vessel associated with vaporizing the vaporized substance. The temperature may be indicative of a vaporization rate of a compound within a vaporization vessel. The vaporization vessel may be one or more of the structures disclosed herein (e.g., vaporization chamber 108 of FIG. 1, vessel 204 of FIG. 2, etc.)

At block 504, processing logic determines a concentration of the vaporized substance within the compound gas based on the first data, the second data, and the third data. The following gas property may be utilized by the processing to take mass flow measurement and calculate the concentration:

$$\text{Vapor pressure} \propto \frac{1}{\text{Molecular weight}} \qquad \text{Equation 1}$$

In some embodiments, the process device looks at the change in density (e.g., Vapor pressure multiplied by molecular weight). For example, a gas may travel through the first flow path with a molecular weight of 28 grams per mole (g/mol). This may be measured by determining at sensor 104 that the first gas is flowing at 250 standard cubic centimeter per minute (sccm) with a pressure of 100 torr. After passing through the vaporization chamber 108 and picking up the vaporized substance in a vaporized substance gas including the first gas (e.g., carrier gas) and the vaporized substance (e.g., precursor) flow through the second flow path. The second sensor may measure an average molecular weight of 30.89 g/mol which is about 10% greater than the carrier gas alone. The average molecular weight may be determine by measuring a flow rate of about 275 sccm and a pressure of 100 torr. The percentage increase of the carrier gas with the vaporized substance is indicative of the concentration of the vaporized substance within the compound gas.

In some embodiments, processing logic inputs the first data indicative of the first mass flow rate, the second data indicative of the second mass flow rate and/or the third data indicative of the temperature of the vaporization vessel to a trained machine learning model that outputs the concentration of the vaporized substance.

It should be noted that the method for calculating concentration is species independent. Conventional concentration sensor like optical sensors should be precalibrated and manufactured to measure predetermined species specification windows such as limits on density, molecular mass, flow rate, etc. The subject matter allowed herein may allow for species independent calculations that can work for various gases (e.g., carrier gases and process gasses) and various compounds (e.g., precursors).

At block 505, processing logic, optionally, modifies a flow rate of the carrier gas. In some embodiments, the processing monitor and controls gas delivery parameters, such as controlling flow rates of gases (e.g., carrier gas or process gas), adjusting the state of the vaporization vessel (e.g., changing temperature, pressure, etc.), and/or carrying out process chamber procedures (e.g., a CVD process or an ALD process). Concentration determination may be incorporated into decisions made by the processing device. For example, if a precursor concentration is higher than a threshold level the processing device may cause a flow of the carrier gas to increase (e.g., opening valve a valve) or cause a flow rate of a vaporizable substance into the vessel to be decreased (e.g., partially closing valves). In some embodiments, the processing device may determine a vaporized substance concentration meets a threshold criteria and cause process operations associated with a process chamber (e.g., a substrate processing chamber) to be modified. For example, process operations within the chamber may cease until the vaporized substance concentration fails to meet the threshold condition. In another example, process steps may be performed under different parameters based on the determine vaporizable substance concentration (e.g., higher temperature, longer etching durations, deposition durations, etc.).

In some embodiments, processing logic inputs the first data indicative of the first mass flow rate, the second data indicative of the second mass flow rate and/or the third data indicative of the temperature of the vaporization vessel to a trained machine learning model that outputs one or more process parameter updates, such as modifications to a flow rate of the carrier gas and/or process gas, a state of the vaporization vessel, and/or other process parameter updates.

At block 506, processing logic, optionally, provides the concentration for display by a graphical user interface (GUI). The concentration may be stored and displayed later as part of a post mortem analysis. In some embodiments, the concentration may be calculated and/or displayed while gas delivery process in undergoing. For example, a concentration of the precursor may be tracked throughout a portion of a substrate processing procedure.

In some embodiments, processing logic, receives, from a fourth sensor, fourth data indicative of a third mass flow rate of a second carrier gas. The compound gas may further include the second carrier gas.

In some embodiments, processing logic, determines a quantity of the vaporized substance disposed within the vaporization vessel based on the determined concentration. The determined vaporized substance quantity may be provided for display by the GUI.

Figure 6:
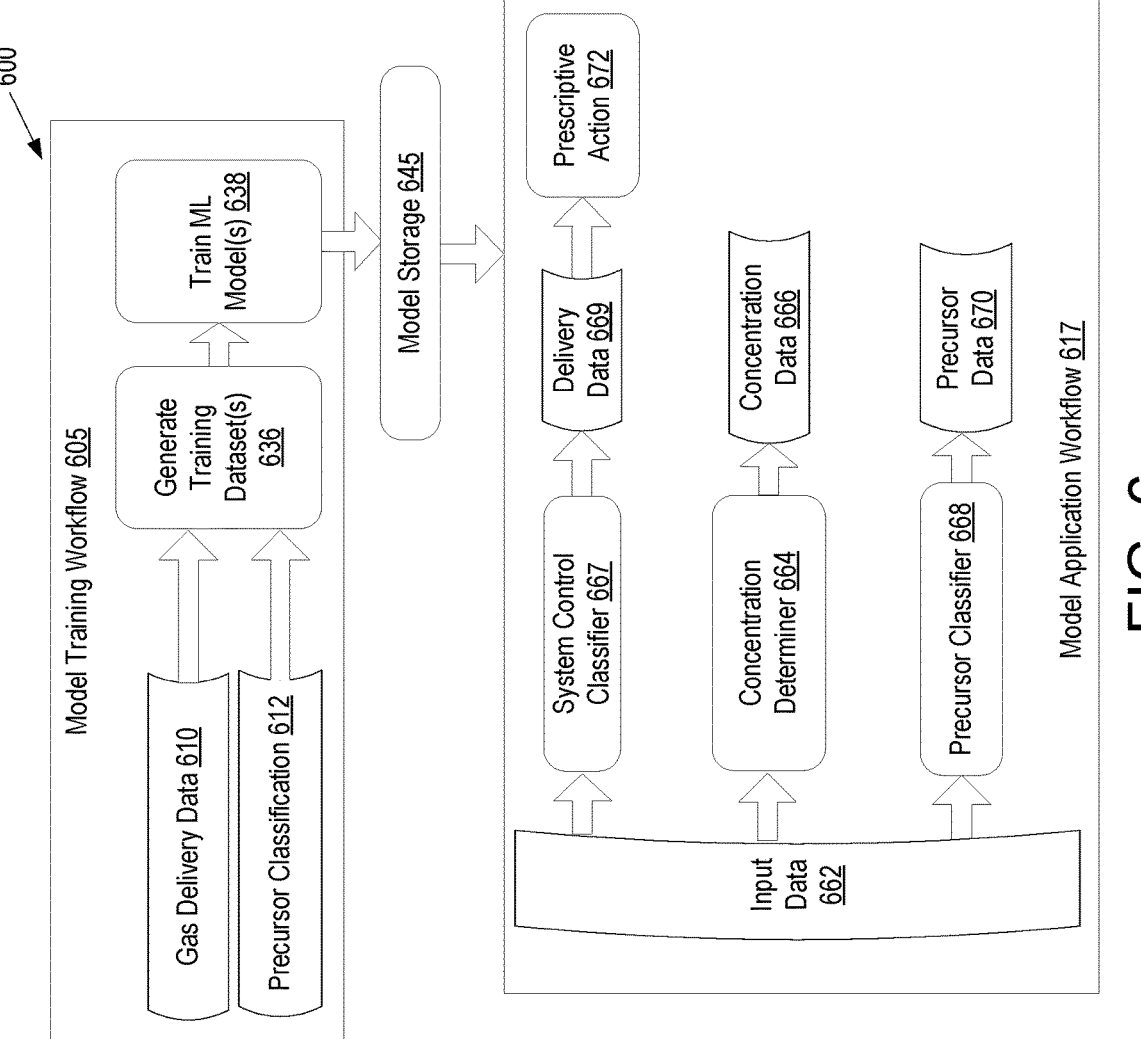
FIG. 6 illustrates a model training workflow and a model application workflow for a concentration sensor, in accordance with an embodiment of the present disclosure.

FIG. 6 illustrates a model training workflow 605 and a model application workflow 617 for a concentration sensor and performing process control based on a detected concentration of a process gas, in accordance with an embodiment of the present disclosure. In embodiments, the model training workflow 605 may be performed at a server which may or may not include a concentration sensor application, and the trained models are provided to a concentration sensor application (e.g., on computing device 222 of FIG. 2), which may perform the model application workflow 617. The model training workflow 605 and the model application workflow 617 may be performed by processing logic executed by a processor of a computing device. One or more of these workflows 605, 617 may be implemented, for example, by one or more machine learning modules implemented in a concentration tool 224, a system control module 226, a precursor monitor 228, and/or other software and/or firmware executing on a processing device of computing device 222 shown in FIG. 2.

The model training workflow 605 is to train one or more machine learning models (e.g., deep learning models) to perform one or more classifying, segmenting, detection, recognition, decision, etc. tasks associated with a concentration sensor (e.g., measuring mass flow rate, calculating concentration, determining precursor data, determining system control data and/or diagnostics, determining modifications to a process, etc.). The model application workflow 617 is to apply the one or more trained machine learning models to perform the classifying, segmenting, detection, recognition, determining, etc. tasks for vaporization data (e.g., mass flow data of a carrier gas, mass flow data of a process gas, precursor quantity and depletion rates, vaporization chamber data etc.). One or more of the machine learning models may receive and process gas delivery data (e.g., molecular mass of one or more relevant gases, mass flow rate of carrier gas, mass flow rate of process gas including the vaporized precursor). One or more of the machine learning models may receive and process vaporization chamber data (e.g., temperature, pressure, mass flow within the chamber, etc.) and precursor data (molecular mass, chemical composition, quantity in the vaporization chamber, depletion rate, etc.).

Various machine learning outputs are described herein. Particular numbers and arrangements of machine learning models are described and shown. However, it should be understood that the number and type of machine learning models that are used and the arrangement of such machine learning models can be modified to achieve the same or similar end results. Accordingly, the arrangements of machine learning models that are described and shown are merely examples and should not be construed as limiting.

In embodiments, one or more machine learning models are trained to perform one or more of the below tasks. Each task may be performed by a separate machine learning model. Alternatively, a single machine learning model may perform each of the tasks or a subset of the tasks. Additionally, or alternatively, different machine learning models may be trained to perform different combinations of the tasks. In an example, one or a few machine learning models may be trained, where the trained ML model is a single shared neural network that has multiple shared layers and multiple higher level distinct output layers, where each of the output layers outputs a different prediction, classification, identification, etc. The tasks that the one or more trained machine learning models may be trained to perform are as follows:

a. Precursor concentration determination—As discussed previously, relationships between flow rate, density, and vaporization may be employed to determine a relative concentration of a precursor within a process gas. A computing device may receive data indicative of flow rate of additional flow path as appropriate and may aggregate this data with first and second data to perform updated concentration calculations and make further determinations such as precursor concentration classification, as described herein. The precursor concentration determination may be associated with air flow hardware configurations (e.g., number of flow paths, splitting and branching of the flow paths, number of precursors, number of carrier gases, etc.). In some embodiments, the precursor concentration determination provides a calibrated b. Precursor concentration classification—as described previously, a computing device may include a precursor monitor that determines a rate of depletion of a precursor within a vaporization vessel. Flow rate and precursor concentration may be used to classify the precursor concentration (e.g., within a threshold bound, above a threshold bound, within a threshold bound but depleting at or above a depletion threshold, etc.)

c. System control classification—as described previously, a computing device may control a gas flow system such as controlling flow rates of gases (e.g., carrier gas or process gas), adjusting the state of the vessel (e.g., changing temperature, pressure, etc.), and/or carrying out process chamber procedures (e.g., a CVD process or an ALD process). The machine learning model may output instructions that may be displayed and/or applied to a gas delivery system such as a remedial or prescriptive action for a vaporization system to undertake. For example, the machine learning module may detect that a precursor concentration is higher than a threshold level and may cause a vaporization system to increase a flow rate of a carrier gas (e.g., such as to dilute or lower the precursor concentration within a process gas.)

One type of machine learning model that may be used to perform some or all of the above tasks is an artificial neural network, such as a deep neural network. Artificial neural networks generally include a feature representation component with a classifier or regression layers that map features to a desired output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In a precursor classification, for example, the raw input may be mass flow measurements of carrier and/or process gasses; the second layer may compose feature data associated with a state of a vaporization chamber; the third layer may include identifying features of the carrier and/or process gas (e.g., molecular weight, density, chemical make-up). Notably, a deep learning process can learn which features to optimally place in which level on its own. The "deep" in "deep learning" refers to the number of layers through which the data is transformed. More precisely, deep learning systems have a substantial credit assignment path (CAP) depth. The CAP is the chain of transformations from input to output. CAPs describe potentially causal connections between input and output. For a feedforward neural network, the depth of the CAPs may be that of the network and may be the number of hidden layers plus one. For recurrent neural networks, in which a signal may propagate through a layer more than once, the CAP depth is potentially unlimited.

In one embodiment, one or more machine learning model is a recurrent neural network (RNN). An RNN is a type of neural network that includes a memory to enable the neural network to capture temporal dependencies. An RNN is able to learn input-output mappings that depend on both a current input and past inputs. The RNN will address past and future flow rate measurements and make predictions based on this continuous metrology information. RNNs may be trained using a training dataset to generate a fixed number of outputs (e.g., to determine a concentration of a vaporizable substance at various point along a flow path of a gas delivery system). One type of RNN that may be used is a long short term memory (LSTM) neural network.

Training of a neural network may be achieved in a supervised learning manner, which involves feeding a training dataset consisting of labeled inputs through the network, observing its outputs, defining an error (by measuring the difference between the outputs and the label values), and using techniques such as deep gradient descent and backpropagation to tune the weights of the network across all its layers and nodes such that the error is minimized. In many applications, repeating this process across the many labeled inputs in the training dataset yields a network that can produce correct output when presented with inputs that are different than the ones present in the training dataset.

For the model training workflow 605, a training dataset containing hundreds, thousands, tens of thousands, hundreds of thousands or more carrier and process gas flow rate measurements (e.g., gas delivery data 610) should be used to form a training dataset. In embodiments, the training dataset may also include an associated precursor classification 612 for forming a training dataset, where each data point and/or associated precursor classification may include various labels or classifications of one or more types of useful information. Each case may include, for example, data indicative of a first flow rate of a carrier gas and a second flow rate of a process gas and a determined precursor classification (e.g., precursor concentration, depletion rate, quantity stored in vaporization chamber, etc.). This data may be processed to generate one or multiple training datasets 636 for training of one or more machine learning models. The machine learning models may be trained, for example, to automate one or more processes of a precursor delivery system (e.g., increasing/decreasing flow rates of carrier and/or process gases, increasing precursor quantity within a vaporization chamber, and other processes associated with delivery a precursor).

In some embodiments, a training dataset containing hundreds, thousands, tens of thousands, hundreds of thousands or more carrier and process flow rate measurements (e.g., gas delivery data 610) is used to form a training dataset. The training data set may also include an associated precursor classification 612 for forming a training dataset. The precursor classification 612 may include one or more concentration measurements (e.g., performed using a residual gas analyzer RGA or other concentration sensor).

In one embodiment, generating one or more training datasets 636 includes gathering one or more gas flow measurement of a carrier gas and a process gas. The labels that are used may depend on what a particular machine learning model will be trained to do. For example, to train a machine learning model to perform precursor classification, a training dataset 636 may include data indicative of a type of gas (e.g., molecular weight, density, etc.), gas flow measurements (e.g., mass flow rates of carrier and/or process gases) and data indicative of a semiconductor processing specifications. For example, a semiconductor process may be associated with a window of precursor concentrations associated with a semiconductor processing result that meets a threshold standard.

To effectuate training, processing logic inputs the training dataset(s) 636 into one or more untrained machine learning models. Prior to inputting a first input into a machine learning model, the machine learning model may be initialized. Processing logic trains the untrained machine learning model(s) based on the training dataset(s) to generate one or more trained machine learning models that perform various operations as set forth above.

Training may be performed by inputting one or more of the gas delivery data 610 and precursor classifications 612 into the machine learning model one at a time. In some embodiments, the training of the machine learning model includes tuning the model to receive gas delivery data 610 (e.g., mass flow rates of a carrier gas and a process gas) and output a precursor concentration prediction (e.g., precursor classification 612) within a threshold difference of a measured precursor concentration (e.g., performed using a residual gas analyzer RGA or other concentration sensor).

The machine learning model processes the input to generate an output. An artificial neural network includes an input layer that consists of values in a data point. The next layer is called a hidden layer, and nodes at the hidden layer each receive one or more of the input values. Each node contains parameters (e.g., weights) to apply to the input values. Each node therefore essentially inputs the input values into a multivariate function (e.g., a non-linear mathematical transformation) to produce an output value. A next layer may be another hidden layer or an output layer. In either case, the nodes at the next layer receive the output values from the nodes at the previous layer, and each node applies weights to those values and then generates its own output value. This may be performed at each layer. A final layer is the output layer, where there is one node for each class, prediction and/or output that the machine learning model can produce.

Accordingly, the output may include one or more predictions or inferences. For example, an output prediction or inference may include a determined concentration of a precursor within a precursor delivery system. Processing logic may then compare the predicted or inferred output to measured or known precursor classification (e.g., measured concentrations) that was included in the training data item. Processing logic determines an error (i.e., a classification error) based on the differences between the output of machine learning model and the known classification (e.g., precursor classification). Processing logic adjusts weights of one or more nodes in the machine learning model based on the error. An error term or delta may be determined for each node in the artificial neural network. Based on this error, the artificial neural network adjusts one or more of its parameters for one or more of its nodes (the weights for one or more inputs of a node). Parameters may be updated in a back propagation manner, such that nodes at a highest layer are updated first, followed by nodes at a next layer, and so on. An artificial neural network contains multiple layers of "neurons", where each layer receives as input values from neurons at a previous layer. The parameters for each neuron include weights associated with the values that are received from each of the neurons at a previous layer. Accordingly, adjusting the parameters may include adjusting the weights assigned to each of the inputs for one or more neurons at one or more layers in the artificial neural network.

Once the model parameters have been optimized, model validation may be performed to determine whether the model has improved and to determine a current accuracy of the deep learning model. After one or more rounds of training, processing logic may determine whether a stopping criterion has been met. A stopping criterion may be a target level of accuracy, a target number of processed images from the training dataset, a target amount of change to parameters over one or more previous data points, a combination thereof and/or other criteria. In one embodiment, the stopping criteria is met when at least a minimum number of data points have been processed and at least a threshold accuracy is achieved. The threshold accuracy may be, for example, 70%, 80% or 90% accuracy. In one embodiment, the stopping criteria is met if accuracy of the machine learning model has stopped improving. If the stopping criterion has not been met, further training is performed. If the stopping criterion has been met, training may be complete. Once the machine learning model is trained, a reserved portion of the training dataset may be used to test the model.

As an example, in one embodiment, a machine learning model (e.g., precursor classifier 668) is trained to determine precursor concentration and/or states of a precursor within a vaporization chamber. A similar process may be performed to train machine learning models to perform other tasks such as those set forth above. A set of many (e.g., thousands to millions) gas delivery measurements (e.g., mass flow rates measurements of carrier gases and/or process gases) may be collected and concentration data 666 associated with predicted or inferred concentrations associated with the input data 662 may be determined.

Once one or more trained machine learning models 638 are generated, they may be stored in model storage 645, and may be added to concentration sensor application (e.g., concentration tool 224, system control module 226, and/or precursor monitor 228). Concentration sensor application may then use the one or more trained ML, models 638 as well as additional processing logic to implement an automatic mode, in which user manual input of information is minimized or even eliminated in some instances.

In one embodiment, model application workflow 617 includes one or more trained machine learning models that function as a system control classifier 667, precursor concentration determiner 664, and/or a precursor classifier 668. These logics may be implemented as separate machine learning models or as a single combined machine learning model in embodiments. For example, system control classifier 667, precursor concentration determiner 664, and precursor classifier 668 may share one or more layers of a deep neural network. However, each of these logics may include distinct higher level layers of the deep neural network that are trained to generate different types of outputs. The illustrated example is shown with only some of the functionality that is set forth in the list of tasks above for convenience. However, it should be understood that any of the other tasks may also be added to the model application workflow 617.

For model application workflow 617, according to one embodiment, input data 662 may be input into system control classifier 667, which may include a trained neural network. Based on the input data 662, system control classifier 667 outputs information indicative of a state of a precursor delivery system (e.g., delivery data 669). This may include outputting a set of classification probabilities for prescriptive actions 672. The prescriptive actions 672 may include actions notified to an controller (e.g., user and/or automated system) that when applied to a gas delivery system alter a state of the precursor delivery system (e.g., lower concentration of precursor within the process gas, lower temperature of vaporization chamber, halts operations, etc.)

According to one embodiment, input data 662 may be input into precursor concentration determiner 664, which may include a trained neural network. Based on the input data 662, precursor concentration determiner 664 outputs a determination of concentration (e.g., concentration data 666) of a precursor within a precursor delivery system associated with the input data 662. For example, the machine learning model may be tuned to receive gas delivery data 610 (e.g., mass flow rates of a carrier gas and a process gas) and output a precursor concentration prediction (e.g., precursor classification 612) within a threshold difference of a measured precursor concentration (e.g., performed using a residual gas analyzer RGA or other concentration sensor) of the same carrier gas and process gas whose mass flow rate is measured and used as input to the precursor concentration determiner 664.

According to one embodiment, input data 662 may be input into precursor classifier 668, which may include a trained neural network. Based on the input data 662, precursor classifier 668 may classify a precursor of a precursor delivery system. For example the output may indicate a depletion rate of a precursor within a vaporization chamber. The output may indicate a quantity of precursor within a vaporization chamber. The output may indicate a chemical composition of the precursor (e.g., a concentration percentage of multiple precursors).

Figure 7:
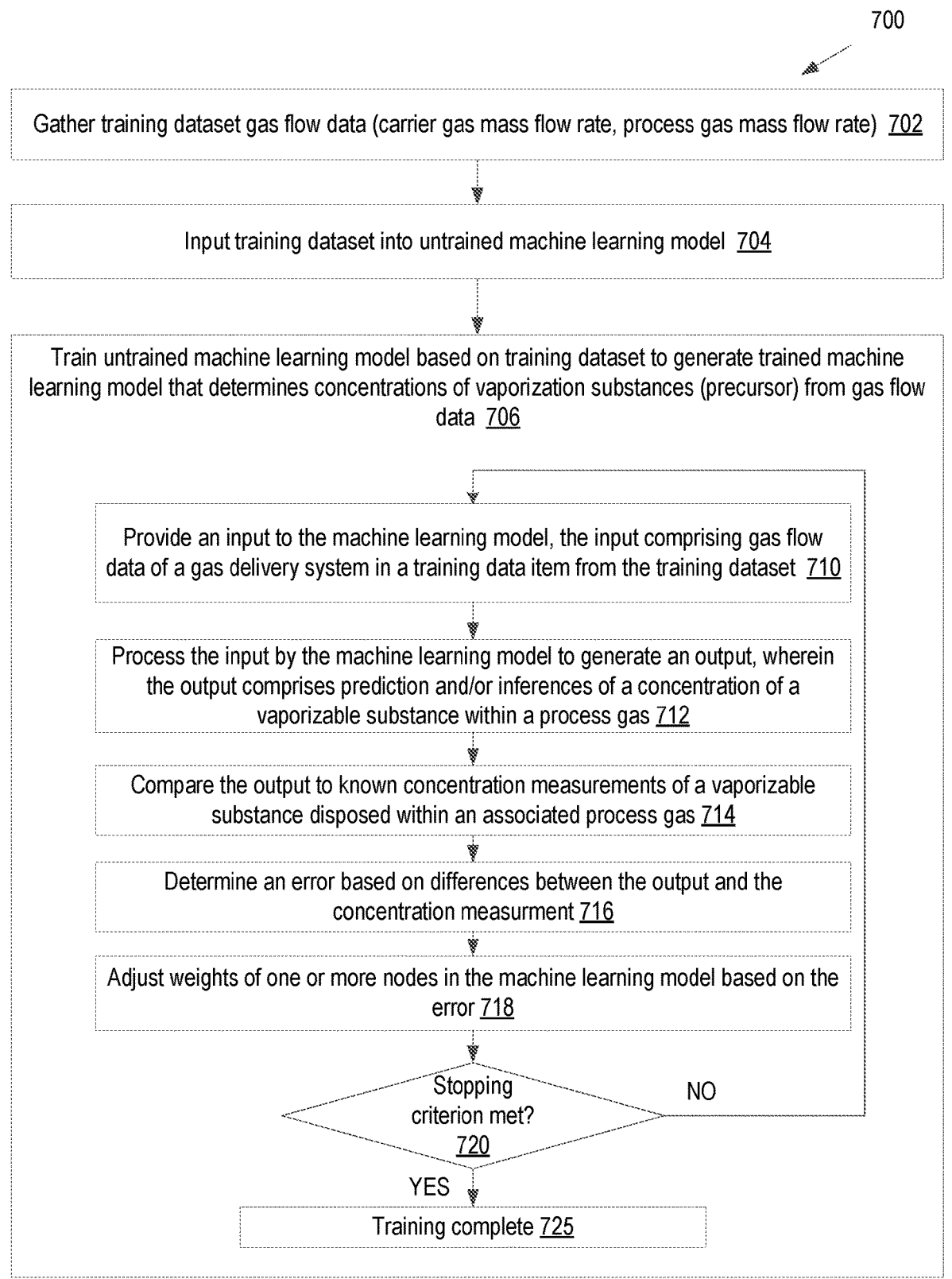
FIG. 7 is a flow chart illustrating an embodiment for a method of training a machine learning model to determine concentration of a vaporizable substance disposed within a process gas, in accordance with an embodiment of the present disclosure.

FIG. 7 is a flow chart illustrating an embodiment for a method 700 of training a machine learning model to determine concentration of a vaporizable substance within a process gas, in accordance with an embodiment of the present disclosure. At block 702 of method 700, processing logic gathers a training dataset, which may include a flow rate (e.g., mass flow rate) of a carrier gas and a process gas within a gas delivery system. Each data item (e.g., carrier gas mass flow rate and/or process gas mass flow rate) of the training dataset may include one or more known concentration levels of a vaporizable substance disposed within the process gas.

At block 704, data items from the training dataset are input into the untrained machine learning model. At block 706, the machine learning model is trained based on the training dataset to generate a trained machine learning model that determines vaporizable substance (e.g., precursors) concentrations within process gases. The machine learning model may also be trained to output one or more other types of predictions, classifications, decisions, and so on. For example, the machine learning model may also be trained to classify a precursor and makes decisions (e.g., manually or automatically performed) to alter an operation of a gas delivery system (e.g., gas delivery system 200 of FIG. 2).

In one embodiment, at block 710 an input of a training data item is input into the machine learning model. The input may include gas flow data of a gas delivery system. At block 712, the machine learning model processes the input to generate an output. The output may include a prediction and/or inference of a concentration of a vaporizable substance (e.g., precursor) within a process gas of a gas delivery system and/or one or more process updates for a manufacturing process that uses the gas delivery system (e.g., to perform an atomic layer deposition process, a chemical vapor deposition process, or other process).

At block 714, processing logic compares the output to a known concentration measurement of a vaporizable substance disposed within an associated process gas. At block 716, processing logic determines an error based on differences between the output and the concentration measurement. At block 718, processing logic adjusts weights of one or more nodes in the machine learning model based on the error.

Additionally, at block 714, processing logic may compare output probabilities of other predictions, classifications, etc. to one or more other labels associated with the input. For example, one or more process parameter updates may be output by the machine learning model, which may be compared to labels of proper process parameters to be used. At block 716, processing logic may determine errors for each of the comparisons. At block 718, processing logic may adjust weights of one or more nodes in the machine learning model based on these errors. Thus, the machine learning model may be trained to perform concentration determination as well as precursor classification and/or one or more other classification, determination or prediction operations.

At block 720, processing logic determines if a stopping criterion is met. If a stopping criterion has not been met, the method returns to block 710, and another training data item is input into the machine learning model. If a stopping criterion is met, the method proceeds to block 725, and training of the machine learning model is complete.

In one embodiment, multiple different ML models are trained to concentration determination, precursor classification, and/or system control classification. Each of the ML models may be trained for determination and/or classification for a different type of input data. For example, a first ML model may be trained to perform concentration determination using mass flow rate measurements of carrier and process gases, a second ML model may be trained to perform concentration determination using data indicative of a state of a vaporization chamber (e.g., temperature, pressure, etc.), and a third ML model may be trained to perform concentration determination using a combination of chamber data and gas flow rate data. In one embodiment, a single ML model is trained to perform the operations of the above discussed first, second and third ML models.

FIG. 8 depicts a flow diagram of one example method for determining a concentration of a vaporizable substance (e.g., precursor) using a trained machine learning model, in accordance with some implementation of the present disclosure. Method 800 is performed by processing logic that may comprise hardware (circuitry, dedicated logic, etc.), software (such as is run on a general purpose computer system or a dedicated machine) or any combination thereof. In one implementation, the method is performed using the computing device 222 and the trained machine learning model 638, while in some other implementations, one or more blocks of FIG. 8 may be performed by one or more other machines not depicted in the figures.

Method 800 may include receiving gas delivery data (e.g., gas flow data described in association with FIGS. 2-4) and processing the gas delivery data using a trained model such as trained machine learning model 638. In some embodiments, the trained model may be configured to generate, based on gas delivery, one or more outputs indicating (i) a predicted concentration of a vaporizable substance disposed within an associated process gas, and (ii) a level of confidence associated with the accuracy of the predicted concentration. In some embodiments, the trained machine learning model may be configured to generate, based on gas delivery, one or more outputs indicating (i) updates to process control parameters, and (ii) a level of confidence that the updates may improve one or more operating conditions of a gas delivery system.

At block 802, gas delivery data associated with a gas delivery system (e.g., gas delivery system 200 of FIG. 2) is identified. The gas delivery data may include data indicative of a first mass flow rate of a carrier gas, a second mass flow rate of a compound gas comprising the carrier gas and a vaporized substance, and/or a temperature of a vaporization vessel associated with vaporizing the vaporized substance.

In some embodiments, the gas delivery data further includes synthetic data, or data engineered from raw sensor data. For example, as described in previous embodiments, various engineering tools can perform a feature extraction and/or create artificial and/or virtual parameter combinations. A feature extractor can create various features by performing variable analysis such as process control analysis, univariate limit violation analysis, and/or multivariate limit violation analysis on raw sensor data.

At block 804, the gas delivery data is provided as input to the trained machine learning model, and at block 806, one or more outputs are obtained from the trained machine learning model. The one or more outputs may include precursor concentrations, precursor classification, and/or process control updates. At block 808, confidence data is extracted from the output(s) obtained at block 806. In one implementation, the confidence data comprises a level of confidence associated with an accuracy of the predicted concentration. In one example, the level of confidence is a real number between 0 and 1 inclusive. It should be noted that the level of confidence may not be a probability (for example, the sum of the confidences levels for the prescriptive actions may not equal 1). At block 810, processing logic determines the level of confidence satisfies a threshold condition.

At block 812, processing logic, optionally, modifies a flow rate of the carrier gas. In some embodiments, the processing monitor and controls gas delivery parameters, such as controlling flow rates of gases (e.g., carrier gas or process gas), adjusting the state of the vaporization vessel (e.g., changing temperature, pressure, etc.), and/or carrying out process chamber procedures (e.g., a CVD process or an ALD process). Concentration determination may be incorporated into decisions made by the processing device. For example, a precursor concentration indication that is higher than a threshold level the processing device may cause a flow of the carrier gas to increase (e.g., opening valve a valve) or cause a flow rate of a vaporizable substance into the vessel to be decreased (e.g., partially closing valves). In some embodiments, processing logic may determine a vaporized substance concentration meets a threshold criteria and cause process operations associated with a process chamber (e.g., a substrate processing chamber) to be modified. For example, process operations within the chamber may cease until the vaporized substance concentration fails to meet the threshold condition. In another example, process steps may be performed under different parameters based on the determine vaporizable substance concentration (e.g., higher temperature, longer etching durations, deposition durations, etc.). In some embodiments, the machine learning outputs the modifications and/or adjustments to a gas delivery system. For example, the machine learning model may indicate a change in flow rate of a gas (e.g., carrier gas and/or process gas).

At block 814, processing logic, optionally, provides the concentration for display by a graphical user interface (GUI). The concentration may be stored and displayed later as part of a post mortem analysis. In some embodiments, the concentration may be calculated and/or displayed while gas delivery process in undergoing. For example, a concentration of the precursor may be tracked throughout a portion of a substrate processing procedure.

Figure 9:
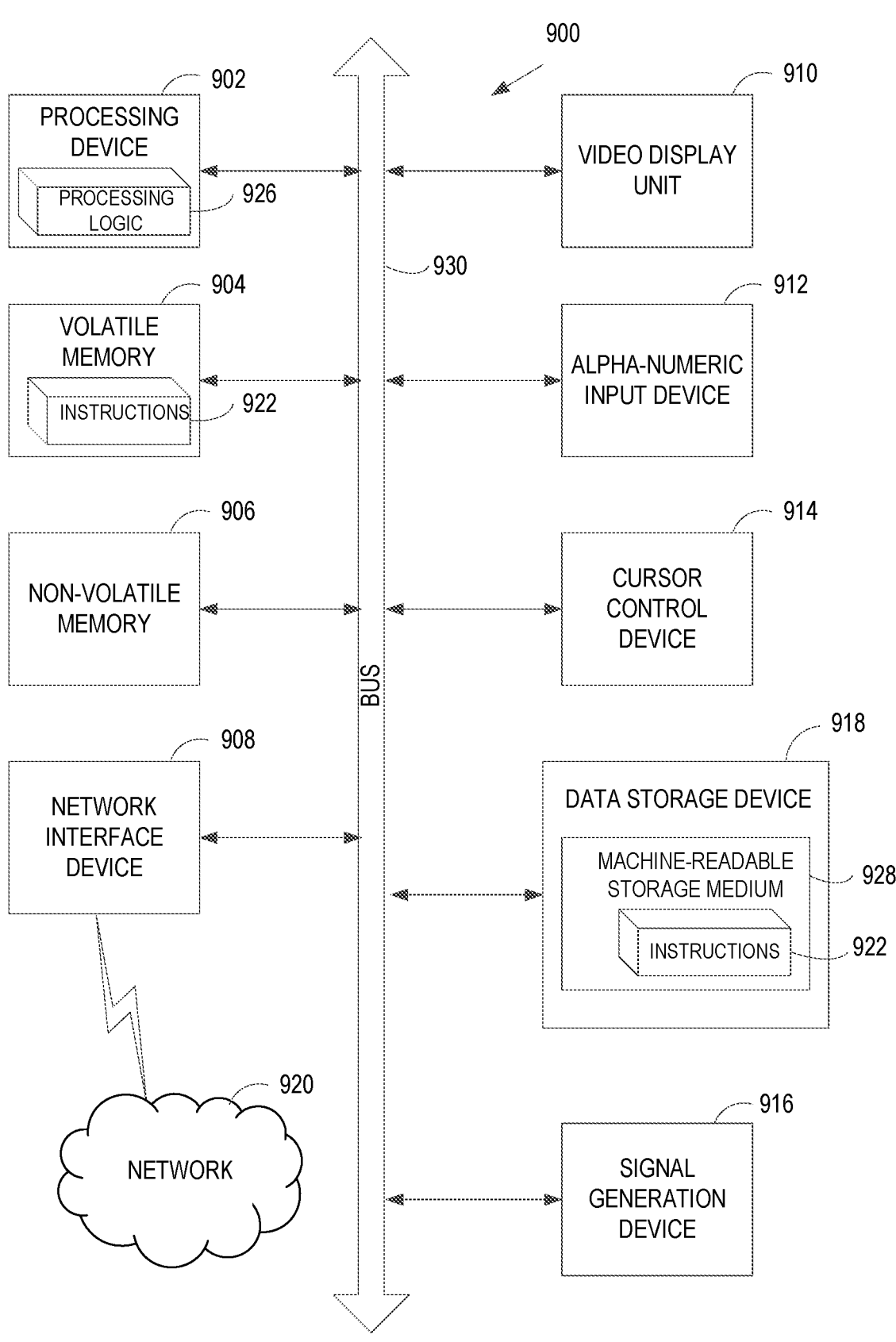
FIG. 9 depicts a block diagram of an example computing device capable of calculating concentrations of gases, operating in accordance with one or more aspects of the disclosure.

FIG. 9 depicts a block diagram of an example computing device capable of calculating concentration of gases, operating in accordance with one or more aspects of the disclosure. In various illustrative examples, various components of the computing device 900 may represent various components of the computing device 222, and/or controller 450.

Example computing device 900 may be connected to other computer devices in a LAN, an intranet, an extranet, and/or the Internet. Computing device 900 may operate in the capacity of a server in a client-server network environment. Computing device 900 may be a personal computer (PC), a set-top box (STB), a server, a network router, switch or bridge, or any device capable of executing a set of instructions (sequential or otherwise) that specify actions to be taken by that device. Further, while only a single example computing device is illustrated, the term "computer" shall also be taken to include any collection of computers that individually or jointly execute a set (or multiple sets) of instructions to perform any one or more of the methods discussed herein.

Example computing device 900 may include a processing device 902 (also referred to as a processor or CPU), a main memory 904 (e.g., read-only memory (ROM), flash memory, dynamic random access memory (DRAM) such as synchronous DRAM (SDRAM), etc.), a static memory 906 (e.g., flash memory, static random access memory (SRAM), etc.), and a secondary memory (e.g., a data storage device 918), which may communicate with each other via a bus 930.

Processing device 902 represents one or more general-purpose processing devices such as a microprocessor, central processing unit, or the like. More particularly, processing device 902 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 902 may also be one or more special-purpose processing devices such as an application specific integrated circuit (ASIC), a field programmable gate array (FPGA), a digital signal processor (DSP), network processor, or the like. In accordance with one or more aspects of the present disclosure, processing device 902 may be configured to execute instructions implementing methods 500 illustrated in FIG. 5.

Example computing device 900 may further comprise a network interface device 908, which may be communicatively coupled to a network 920. Example computing device 900 may further comprise a video display 910 (e.g., a liquid crystal display (LCD), a touch screen, or a cathode ray tube (CRT)), an alphanumeric input device 912 (e.g., a keyboard), a cursor control device 914 (e.g., a mouse), and an acoustic signal generation device 916 (e.g., a speaker).

Data storage device 918 may include a machine-readable storage medium (or, more specifically, a non-transitory machine-readable storage medium) 928 on which is stored one or more sets of executable instructions 922. In accordance with one or more aspects of the present disclosure, executable instructions 922 may comprise executable instructions associated with executing methods 500-800 illustrated in FIGS. 5-8.

Executable instructions 922 may also reside, completely or at least partially, within main memory 904 and/or within processing device 902 during execution thereof by example computing device 900, main memory 904 and processing device 902 also constituting computer-readable storage media. Executable instructions 922 may further be transmitted or received over a network via network interface device 908.

While the computer-readable storage medium 928 is shown in FIG. 9 as a single medium, the term "computer-readable storage medium" should be taken to include a single medium or multiple media (e.g., a centralized or distributed database, and/or associated caches and servers) that store the one or more sets of operating instructions. The term "computer-readable storage medium" shall also be taken to include any medium that is capable of storing or encoding a set of instructions for execution by the machine that cause the machine to perform any one or more of the methods described herein. The term "computer-readable storage medium" shall accordingly be taken to include, but not be limited to, solid-state memories, and optical and magnetic media.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a target result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "identifying," "determining," "storing," "adjusting," "causing," "returning," "comparing," "creating," "stopping," "loading," "copying," "throwing," "replacing," "performing," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Examples of the present disclosure also relate to an apparatus for performing the methods described herein. This apparatus may be specially constructed for the intended purposes, or it may be a general purpose computer system selectively programmed by a computer program stored in the computer system. Such a computer program may be stored in a computer readable storage medium, such as, but not limited to, any type of disk including optical disks, compact disc read only memory (CD-ROMs), and magnetic-optical disks, read-only memories (ROMs), random access memories (RAMs), erasable programmable read-only memory (EPROMs), electrically erasable programmable read-only memory (EEPROMs), magnetic disk storage media, optical storage media, flash memory devices, other type of machine-accessible storage media, or any type of media suitable for storing electronic instructions, each coupled to a computer system bus.

The methods and displays presented herein are not inherently related to any particular computer or other apparatus. Various general purpose systems may be used with programs in accordance with the teachings herein, or it may prove convenient to construct a more specialized apparatus to perform the recited method steps. The structure for a variety of these systems will appear as set forth in the description below. In addition, the scope of the present disclosure is not limited to any particular programming language. It will be appreciated that a variety of programming languages may be used to implement the teachings of the present disclosure.

It is to be understood that the above description is intended to be illustrative, and not restrictive. Many other implementation examples will be apparent to those of skill in the art upon reading and understanding the above description. Although the present disclosure describes specific examples, it will be recognized that the systems and methods of the present disclosure are not limited to the examples described herein, but may be practiced with modifications within the scope of the appended claims. Accordingly, the specification and drawings are to be regarded in an illustrative sense rather than a restrictive sense. The scope of the present disclosure should, therefore, be determined with reference to the appended claims, along with the full scope of equivalents to which such claims are entitled.

What is claimed is:

1. A method, comprising:

receiving first sensor data indicative of a first mass flow rate of a first gas flowing to a vaporization chamber, the vaporization chamber comprising a compound to be transitioned into a gaseous state;

receiving second sensor data indicative of a second mass flow rate of a second gas flowing out of the vaporization chamber, wherein the second gas comprises the compound and the first gas;

receiving third sensor data indicative of a third mass flow rate of the compound into the vaporization chamber;

determining an estimated concentration of the compound within the second gas based on processing the first sensor data, the second sensor data, and the third sensor data; and modifying a flow rate of the first gas based on the estimated concentration of the compound within the second gas.

2. The method of claim 1, wherein at least one of the first sensor data, the second sensor data, or the third sensor data is received from a mass flow rate controller.

3. The method of claim 1, further comprising:

selectively opening and closing a first valve to modify the first mass flow rate of the first gas.

4. The method of claim 1, further comprising:

selectively opening and closing a second valve to modify the second mass flow rate of the second gas.

5. The method of claim 1, further comprising:

determining a depletion rate of the compound within the vaporization chamber based on the estimated concentration of the compound in the second gas.

6. The method of claim 1, further comprising:

receiving fourth sensor data indicative of a temperature of the vaporization chamber; and determining the estimated concentration of the compound within the second gas based on processing the fourth sensor data along with the first sensor data, the second sensor data, and the third sensor data.

7. The method of claim 1, further comprising:

training an untrained machine learning model to produce a trained machine learning model for processing the first sensor data, the second sensor data, and the third sensor data, wherein the untrained machine learning model is trained using a training data set comprising a plurality of flow rate values for the first gas, for the second gas, and for the compound, and a plurality of associated compound concentration values.

8. A method, comprising:

receiving first sensor data indicative of a first mass flow rate of a first gas flowing to a vaporization chamber, the vaporization chamber comprising a compound to be transitioned into a gaseous state;

receiving second sensor data indicative of a second mass flow rate of a second gas flowing out of the vaporization chamber, wherein the second gas comprises the compound and the first gas;

receiving third sensor data indicative of a third mass flow rate of the compound into the vaporization chamber; and training an untrained machine learning model to produce a trained machine learning model, wherein the untrained machine learning model is trained using the first sensor data, the second sensor data, and the third sensor data, and wherein the trained machine learning model is trained to determine an estimated concentration of the compound within the second gas.

9. The method of claim 8, wherein training the untrained machine learning model comprises:

inputting the first sensor data, the second sensor data, and the third sensor data into the untrained machine learning model;

receiving an output from the untrained machine learning model comprising a predicted concentration;

comparing the predicted concentration to a known concentration associated with the first sensor data, the second sensor data, and the third sensor data;

determining an error based on a difference between the predicted concentration and the known concentration; and adjusting one or more weights of one or more nodes of the untrained machine learning model based on the error.

10. The method of claim 8, wherein the trained machine learning model is further trained to classify the compound based on the first sensor data, the second sensor data, and the third sensor data.

11. The method of claim 8, wherein the trained machine learning model is further trained to output an estimated depletion rate of the compound within the vaporization chamber based on the first sensor data, the second sensor data, and the third sensor data.

12. A non-transitory machine-readable storage medium comprising instructions that, when executed by a processing device, cause the processing device to:

receive first sensor data indicative of a first mass flow rate of a first gas flowing to a vaporization chamber, the vaporization chamber comprising a compound to be transitioned into a gaseous state;

receive second sensor data indicative of a second mass flow rate of a second gas flowing out of the vaporization chamber, wherein the second gas comprises the compound and the first gas;

receive third sensor data indicative of a third mass flow rate of the compound into the vaporization chamber;

determine an estimated concentration of the compound within the second gas based on processing the first sensor data, the second sensor data, and the third sensor data; and modify a flow rate of the first gas based on the estimated concentration of the compound within the second gas.

13. The non-transitory machine-readable storage medium of claim 12, wherein at least one of the first sensor data, the second sensor data, or the third sensor data is received from a mass flow rate controller.

14. The non-transitory machine-readable storage medium of claim 12, wherein the processing device is further to:

selectively open and close a first valve to modify the first mass flow rate of the first gas.

15. The non-transitory machine-readable storage medium of claim 12, wherein the processing device is further to:

selectively open and close a second valve to modify the second mass flow rate of the second gas.

16. The non-transitory machine-readable storage medium of claim 12, wherein the processing device is further to:

determine a depletion rate of the compound within the vaporization chamber based on the estimated concentration of the compound in the second gas.

17. The non-transitory machine-readable storage medium of claim 12, wherein the processing device is further to:

receive fourth sensor data indicative of a temperature of the vaporization chamber; and determine the estimated concentration of the compound within the second gas based on processing the fourth sensor data along with the first sensor data, the second sensor data, and the third sensor data.

18. The non-transitory machine-readable storage medium of claim 12, wherein the processing device is further to:

train an untrained machine learning model to produce a trained machine learning model for processing the first sensor data, the second sensor data, and the third sensor data, wherein the untrained machine learning model is trained using a training data set comprising a plurality of flow rate values for the first gas, for the second gas, and for the compound, and a plurality of associated compound concentration values.

19. The non-transitory machine-readable storage medium of claim 18, wherein the trained machine learning model is trained to determine the estimated concentration of the compound within the second gas.

20. The non-transitory machine-readable storage medium of claim 18, wherein the processing device is further to:

input the training data set into the untrained machine learning model;

receive an output from the untrained machine learning model comprising a predicted concentration;

compare the predicted concentration to a known concentration associated with the training data set;

determine an error based on a difference between the predicted concentration and the known concentration; and adjust one or more weights of one or more nodes of the untrained machine learning model based on the error.

\* \* \* \* \*